(12) United States Patent
Dhingra et al.

(10) Patent No.: US 8,709,419 B2
(45) Date of Patent: Apr. 29, 2014

(54) COMBINATION THERAPY

(75) Inventors: Kapil Dhingra, Sparta, NJ (US); Brian Higgins, Fresh Meadows, NY (US); Kenneth Kolinsky, Bloomingdale, NJ (US); Richard J. Lee, Montclair, NJ (US); Brian Lestini, Union City, NJ (US); Kathryn Packman, Bloomfield, NJ (US); Fei Su, Paramus, NJ (US)

(73) Assignee: Hoffmann-La Roche, Inc., Nutley, NJ (US)

( * ) Notice: Subject to any disclaimer, the term of this patent is extended or adjusted under 35 U.S.C. 154(b) by 228 days.

(21) Appl. No.: 13/206,557

(22) Filed: Aug. 10, 2011

(65) Prior Publication Data

US 2012/0045434 A1    Feb. 23, 2012

Related U.S. Application Data

(60) Provisional application No. 61/374,296, filed on Aug. 17, 2010.

(51) Int. Cl.
*A61K 39/00* (2006.01)
*A61K 31/517* (2006.01)
*A61K 31/44* (2006.01)

(52) U.S. Cl.
USPC .............. 424/133.1; 514/266.4; 514/283; 514/300

(58) Field of Classification Search
USPC .............. 424/133.1; 514/266.4, 283, 300
See application file for complete search history.

(56) References Cited

U.S. PATENT DOCUMENTS

| 5,516,807 | A * | 5/1996 | Hupe et al. ............... 514/673 |
| 7,504,509 | B2 | 3/2009 | Ibrahim et al. |
| 7,851,626 | B2 | 12/2010 | Ding et al. |
| 7,863,288 | B2 | 1/2011 | Ibrahim et al. |
| 8,143,271 | B2 | 3/2012 | Ibrahim et al. |
| 8,470,818 | B2 | 6/2013 | Ibrahim et al. |
| 2001/0041712 | A1 | 11/2001 | Bissery |
| 2002/0035091 | A1 | 3/2002 | Govindarajan et al. |
| 2002/0119955 | A1 | 8/2002 | Doyle et al. |
| 2003/0147945 | A1 | 8/2003 | Tardi et al. |
| 2003/0229112 | A1 | 12/2003 | Houghton |
| 2004/0254210 | A1 | 12/2004 | Haeberlin et al. |
| 2005/0176740 | A1* | 8/2005 | Spector et al. ........... 514/264.11 |
| 2005/0244407 | A1 | 11/2005 | Rose |
| 2005/0272737 | A1 | 12/2005 | Chen et al. |
| 2005/0276851 | A1 | 12/2005 | Cunningham et al. |
| 2006/0257400 | A1 | 11/2006 | Fargnoli |
| 2007/0281041 | A1 | 12/2007 | Ramesh et al. |
| 2008/0193445 | A1 | 8/2008 | Goetsch et al. |
| 2008/0248038 | A1 | 10/2008 | Corvinus et al. |
| 2009/0053206 | A1 | 2/2009 | Kandimalla et al. |
| 2009/0214562 | A1 | 8/2009 | Karel |
| 2009/0269344 | A1 | 10/2009 | Siena et al. |
| 2010/0104567 | A1 | 4/2010 | Shiotsu et al. |
| 2010/0152190 | A1 | 6/2010 | Bartkovitz et al. |
| 2010/0297080 | A1 | 11/2010 | Bertelsen et al. |
| 2010/0310659 | A1 | 12/2010 | Desai et al. |
| 2012/0045433 | A1 | 2/2012 | Dhingra et al. |
| 2012/0148533 | A1 | 6/2012 | Dhingra et al. |
| 2013/0245039 | A1 | 9/2013 | Higgins et al. |

FOREIGN PATENT DOCUMENTS

| WO | 2007/002325 | 1/2007 |
| WO | 2008/082730 | 7/2008 |
| WO | 2010/114928 A2 | 10/2010 |
| WO | 2010/114928 A3 | 10/2010 |
| WO | 2010/120759 A1 | 10/2010 |
| WO | 2011/028540 A1 | 3/2011 |
| WO | 2012/022677 A2 | 2/2012 |
| WO | 2012/022724 A1 | 2/2012 |

OTHER PUBLICATIONS

Cunningham et al., "Cetuximab Monotherapy and Cetuximab Plus Irinotecan in Irinotecan-Refractory Metastatic Colorectal Cancer" *N. Eng. J. Med.* 351:337-345 (Jul. 22, 2004).

Dummer et al., "Randomized Dose-Escalation Study Evaluating Peginterferon Alfa-2a in Patients With Metastatic Malignant Melanoma" *J. Clin. Oncol* 24(7):1188-1194 (Mar. 1, 2006).

Friesen et al., "Hydroxypropyl Methylcellulose Acetate Succinate-Based Spray-Dried Dispersions: an Overview," *Mol. Pharm* 5(6):1003-1019 (2008).

Galal et al., "Inherent Resistance to Epidermal Growth Factor Receptor Antibodies in Refractory Metastatic Colorectal Cancer" *J. Med. Sci.* 9(4):165-174 (May 15, 2009).

Goldstein et al., "The Role of Interferon in Cancer Therapy: A Current Perspective" *CA Cancer J. Clin.* 38(5):258-277 (1988).

Huh, et al., "A Review of US Anthropometric Reference Data (1971-2000) With Comparisons to Both Stylized and Tomographic Anatomic Models" *Phys. Med. Biol.* 48(20):3411-3429 (Oct. 21, 2003).

International Search Report mailed on Oct. 17, 2011, for PCT Patent Application No. PCT/EP2011/063892 filed on Aug. 12, 2011, four pages.

(Continued)

*Primary Examiner* — Gina C Justice
*Assistant Examiner* — Genevieve S Alley
(74) *Attorney, Agent, or Firm* — Morrison & Foerster LLP

(57) ABSTRACT

The present invention relates to a combination therapy of propane-1-sulfonic acid {3-[5-(4-chloro-phenyl)-1H-pyrrolo[2,3-b]pyridine-3-carbonyl]-2,4-difluoro-phenyl}-amide, or a pharmaceutically acceptable salt thereof, and an EGFR inhibitor for treating a patient suffering from a proliferative disorder, in particular a solid tumor, for example, colorectal cancer, melanoma, and thyroid cancer.

22 Claims, 9 Drawing Sheets

(56) References Cited

OTHER PUBLICATIONS

International Search Report mailed on Apr. 2, 2012, for PCT Patent Application No. PCT/EP2011/072408 filed on Dec. 12, 2011, five pages.
Lee, et al., "MEK'ing the Most of p53 Reactivation Therapy in Melanoma" *J. Investigative Dermatology* 132:263-265 (2012).
Mross et al., "Results From an in Vitro and a Clinical/Pharmacological Phase I Study With the Combination Irinotecan and Sorafenib" *European Journal of Cancer* 43:55-63 (2007).
Paraiso et al., "The HSP90 Inhibitor XL888 Overcomes BRAF Inhibitor Resistance Mediated through Diverse Mechanisms" *Clin. Cancer. Res.* 18(9):2502-2514 (May 1, 2012, e-pub. Feb. 20, 2012).
Shi et al., "Combinatorial Treatments That Overcome PDGFRβ-Driven Resistance of Melanoma Cells to $^{V600E}$EB-RAF Inhibition" *Cancer Res* 71:5067-5074 (2011).
Written Opinion of the International Searching Authority mailed on Oct. 17, 2011, for PCT Patent Application No. PCT/EP2011/063892 filed on Aug. 12, 2011, seven pages.
Written Opinion of the International Searching Authority mailed on Oct. 20, 2011, for PCT Patent Application No. PCT/EP2011/064050 filed on Aug. 16, 2011, eight pages.
Written Opinion of the International Searching Authority mailed on Apr. 2, 2012, for PCT Patent Application No. PCT/EP2011/072408 filed on Dec. 12, 2011, five pages.
Search Report mailed on Jul. 20, 2013, for Taiwanese Patent Application No. 100129120 filed on Aug. 15, 2011, one page (Jul. 20, 2013).
Kim et al., "Clinical Cancer Research" 12(2):600-607 (2006).
Rubinstein et al., "Journal of Translational Medicine" 8:67-69 (2010).
Salerno et al., "Journal of Clinical Endocrinology Metabolism" 95(1):450-455 (2009).
Abal et al., "Oncogene" 23:1737-1744 (2004).
Ouchi et al., "Cancer Chemotherapy Pharmacology" 57:693-702 (2006).
"International Search Report PCT/EP2011/064050 mailed Oct. 20, 2011".
Chan et al., "Current Opinion of Immunology" 8:394-401 (1996).
Tabernero et al., "The Oncologist" 13(2):113-119 (2008).
Yang et al., "Cancer Research" 70(13):5518-5527 (2010).
Wright et al., "British Journal of Cancer" 65:118-121 (1992).
Prewett et al., "Clinical Cancer Research" 8(5):994-1003 (2002).
Mason, E. (Oct. 23, 2008). "Study Finds BRAF Mutations in Colorectal Cancer Cause Resistance to Anti-EGFR Therapy," *Ecco—The European Cancer Organisation*, 2 Total Pages.

* cited by examiner

COMBINATION THERAPY

PRIORITY TO RELATED APPLICATIONS

This application claims the benefit of U.S. Provisional Application No. 61/374,296, filed Aug. 17, 2010, which is hereby incorporated by reference in its entirety.

FIELD OF THE INVENTION

The present invention relates to a combination therapy for treating a patient suffering from a proliferative disorder, in particular a solid tumor, for example, colorectal cancer, melanoma, and thyroid cancer, comprising administering to the patient propane-1-sulfonic acid {3-[5-(4-chloro-phenyl)-1H-pyrrolo[2,3-b]pyridine-3-carbonyl]-2,4-difluoro-phenyl}-amide and a EGFR inhibitor.

BACKGROUND OF THE INVENTION

Normally functioning b-Raf is a kinase which is involved in the relay of signals from the cell membrane to the nucleus and is active only when it is needed to relay such signals. Mutant b-Raf having the V600E mutation, however, is constantly active and thus plays a role in tumor development. Such mutant b-Raf has been implicated in various tumors, for example, colorectal cancer, melanoma, and thyroid cancer.

Propane-1-sulfonic acid {3-[5-(4-chloro-phenyl)-1H-pyrrolo[2,3-b]pyridine-3-carbonyl]-2,4-difluoro-phenyl}-amide (hereafter also referred to as "Compound I") is a b-raf kinase inhibitor that specifically targets mutant b-Raf having the V600E mutation. This compound is described in WO 2007/002325. Accordingly, such an inhibitor is used in the inhibition of tumors, particularly solid tumors, for example, colorectal cancer, melanoma, and thyroid cancer, which comprise b-Raf having the V600E mutation.

Protein tyrosine kinases (PTKs) catalyze the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394-401). Such PTKs can be divided into receptor tyrosine kinases (e.g. EGFR/HER-1, c-erbB-2/HER-2, c-met, PDGFr, FGFr) and non-receptor tyrosine kinases (e.g. src, lck).

It is known that receptor tyrosine kinases of the HER-family like HER-2 and EGFR (HER-1) are frequently aberrantly expressed in common human cancers such as breast cancer, gastrointestinal cancer (colon, rectal or stomach cancer), thyroid, leukemia and ovarian, bronchial and pancreatic cancer and melanoma. High levels of these receptors correlate with poor prognosis and response to treatment (Wright, C., et al., Br. J. Cancer 65 (1992) 118-121).

Inhibitors of PTKs, and in particular of EGFR, have been developed. Tumors comprising b-Raf having the V600E mutation, however, have been known to be resilient to treatment with EGFR inhibitors. See Prewett et al., Clin. Cancer Res. (2002), 8:994-1003 and Ouchi et al., Cancer Chemother. Pharmacol. (2006), 57:693-702. Applicants have unexpectedly found, however, that combination therapy with Compound I and an EGFR inhibitor not only is capable of reducing such resilience but also results in improved antineoplastic effects that are significantly superior to the results obtained with each compound alone without a significant increase in toxicity.

In addition to EGFR inhibitors, topoisomerase inhibitors are also antiproliferative agents. Tumors containing the V600E mutation, however, have also been known to be resilient to treatment with topoisomerase inhibtors. See Prewett et al., Clin. Cancer Res. (2002), 8:994-1003 and Abal et al., Oncogene (2004), 23:1737-44. Applicants have unexpectedly found, however, that the combination of Compound I with an EGFR inhibitor and a topoisomerase inhibitor not only is capable of reducing such resilience but also results in improved antineoplastic effects that are significantly superior to the results obtained with each compound alone or with the aforementioned combination therapy of Compound I and EGFR inhibitor without a significant increase in toxicity.

SUMMARY OF THE INVENTION

The present invention relates to a method of treating a patient suffering from a proliferative disorder, comprising administering to the patient: (A) a first component which comprises, as an active agent, Compound I, or a pharmaceutically-acceptable salt thereof; and (B) a second component which comprises, as an active agent, an EGFR inhibitor; the amount of said active agents being such that the combination thereof is therapeutically-effective in the treatment of said proliferative disorder.

The present invention also relates to a kit comprising: (A) a first component which comprises, as an active agent, Compound I, or a pharmaceutically-acceptable salt thereof; and (B) a second component which comprises, as an active agent, an EGFR inhibitor.

The present invention further relates to a composition comprising: (A) a first component which comprises, as an active agent, Compound I, or a pharmaceutically-acceptable salt thereof; and (B) a second component which comprises, as an active agent, an EGFR inhibitor.

In addition, the present invention relates to the use of Compound I, or a pharmaceutically-acceptable salt thereof, and an EGFR inhibitor for the treatment of a proliferative disorder.

A yet further aspect of the present invention is the use of Compound I, or a pharmaceutically-acceptable salt thereof, and an EGFR inhibitor for the preparation of a medicament for the treatment of a proliferative disorder.

DETAILED DESCRIPTION OF THE INVENTION

Figure 1:
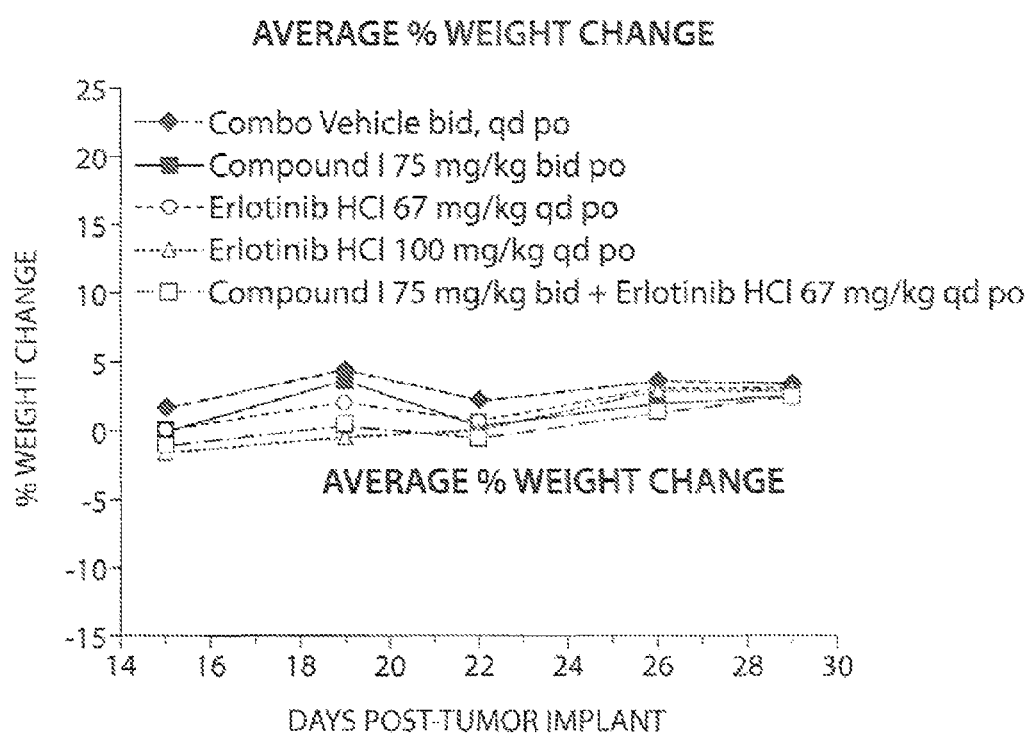
FIG. 1 illustrates the tolerability, as demonstrated by % body weight change, of Compound I monotherapy at 75 mg/kg bid, erlotinib hydrochloride monotherapy at 67 mg/kg qd, erlotinib hydrochloride monotherapy at 100 mg/kg qd, and Compound I at 75 mg/kg bid and erlotinib hydrochloride at 67 mg/kg qd combination therapy.

As stated above, "Compound I" shall herein refer to propane-1-sulfonic acid {3-[5-(4-chloro-phenyl)-1H-pyrrolo[2,3-b]pyridine-3-carbonyl]-2,4-difluoro-phenyl}-amide. This is a compound having the following structure.

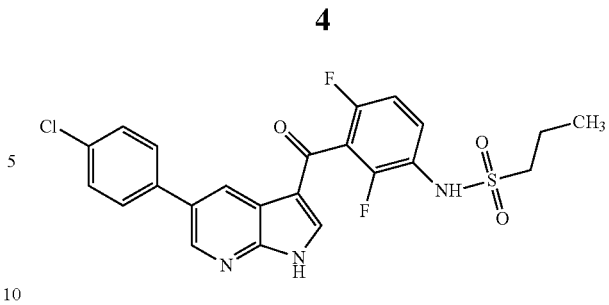

Compound I is a b-Raf kinase inhibitor that specifically targets b-Raf having the V600E mutation.

The "V600E" mutation of b-Raf, as used herein, refers to a mutation in the b-Raf protein wherein the valine residue at residue position 600 of b-Raf is replaced by glutamic acid.

As used herein, when referring to the receptor tyrosine kinases of the HER-family like HER-2 and EGFR (HER-1), the acronym "HER" refers to human epidermal receptor and the acronym "EGFR" refers to epidermal growth factor receptor.

As used herein, the term "pharmaceutically acceptable carrier" indicates that the indicated carrier does not have properties that would cause a reasonably prudent medical practitioner to avoid administration thereof to a patient, taking into consideration the disease or conditions to be treated and the respective route of administration.

As used herein, the term "pharmaceutically acceptable salt" of a compound refers to any conventional salt or base addition salt that retains the biological effectiveness and properties of the compound and which is formed from a suitable non-toxic organic or inorganic acid or organic or inorganic base. As used herein, the term "therapeutically effective" means an amount of drug, or combination or composition, which is effective for producing a desired therapeutic effect upon administration to a patient, for example, to stem the growth, or result in the shrinkage, of a cancerous tumor or to increase the patient's life span.

The terms "cell proliferative disorder" and "proliferative disorder" refer to disorders that are associated with some degree of abnormal cell proliferation. In one embodiment, the proliferative disorder is cancer.

The terms "cancer" and "cancerous" refer to or describe the physiological condition in mammals that is typically characterized by unregulated cell growth/proliferation. Examples of cancer include, but are not limited to, colorectal cancer, melanoma, and thyroid cancer.

The term "colorectal tumor" or "colorectal cancer" refers to any tumor or cancer of the large bowel, which includes the colon (the large intestine from the cecum to the rectum) and the rectum, including, e.g., adenocarcinomas and less prevalent forms, such as lymphomas and squamous cell carcinomas.

"Inhibiting cell growth or proliferation" means decreasing a cell's growth or proliferation by at least 10%, 20%, 30%, 40%, 50%, 60%, 70%, 80%, 90%, 95%, or 100%, and includes inducing cell death.

The phrase "substantially reduced" or "substantially different," as used herein, refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

"Regression" of a tumor is said to occur following treatment when the volume of said tumor is reduced. If the tumor remains present (tumor volume >0 mm$^3$) but its volume is reduced from what it was at the initiation of treatment, "partial regression" (PR) is said to have occurred. If the tumor is palpably absent following treatment, "complete regression" (CR) is said to have occurred.

The present invention relates to a method of treating a patient suffering from a proliferative disorder, comprising administering to the patient: (A) a first component which comprises, as an active agent, Compound I, or a pharmaceutically-acceptable salt thereof; and (B) a second component which comprises, as an active agent, an EGFR inhibitor; the amount of said active agents being such that the combination thereof is therapeutically-effective in the treatment of said proliferative disorder.

Treatment of a proliferative disorder shall be understood to include maintaining or decreasing tumor size, inducing tumor regression (either partial or complete), inhibiting tumor growth, and/or increasing the life span of a patient suffering from said disorder. The present invention also relates to a kit or a composition comprising: (A) a first component which comprises, as an active agent, Compound I, or a pharmaceutically-acceptable salt thereof; and (B) a second component which comprises, as an active agent, an EGFR inhibitor. The kit or composition may be used, for example, in the treatment of a proliferative disorder.

In an embodiment of the invention, the proliferative disorder is a solid tumor.

In another embodiment of the invention, the proliferative disorder is a tumor comprising b-Raf having the V600E mutation.

In a further embodiment of the invention, the proliferative disorder is selected from the group consisting of colorectal cancer, melanoma, and thyroid cancer and the cancer involves a tumor comprising b-Raf having the V600E mutation.

In yet a further embodiment of the invention, the proliferative disorder is a solid tumor comprising b-Raf having the V600E mutation.

In yet a further embodiment of the invention, the proliferative disorder is colorectal cancer.

In yet a further embodiment of the invention, the proliferative disorder is colorectal cancer involving a tumor comprising b-Raf having the V600E mutation.

In yet a further embodiment of the invention, the EGFR inhibitor is a small molecule EGFR inhibitor. In one such embodiment, the EGFR inhibitor is erlotinib, or a pharmaceutically acceptable salt thereof, for example, erlotinib hydrochloride (erlotinib HCl). Erlotinib HCl is sold as Tarceva® by Genentech, South San Francisco, USA.

In yet a further embodiment of the invention, the EGFR inhibitor is a large molecule EGFR inhibitor, for example, an antibody that targets EGFR. In one such embodiment, the EGFR inhibitor may be a monoclonal antibody that targets EGFR, for example, cetuximab. Cetuximab is sold as Erbitux® by ImClone Systems, Inc., New York, U.S.A.

In yet a further embodiment of the invention, the present invention relates to a method of treating a patient suffering from colorectal cancer involving a tumor comprising b-Raf having the V600E mutation, wherein said method comprises administering to the patient: (A) a first component which comprises, as an active agent, Compound I, or a pharmaceutically-acceptable salt thereof; and (B) a second component which comprises, as an active agent, erlotinib, or a pharmaceutically acceptable salt thereof; the amount of said active agents being such that the combination thereof is therapeutically-effective in the treatment of said cancer.

In yet a further embodiment of the invention, the present invention relates to a method of treating a patient suffering from colorectal cancer involving a tumor comprising b-Raf having the V600E mutation, wherein said method comprises administering to the patient: (A) a first component which comprises, as an active agent, Compound I, or a pharmaceutically-acceptable salt thereof; and (B) a second component which comprises, as an active agent, cetuximab; the amount of said active agents being such that the combination thereof is therapeutically-effective in the treatment of said cancer.

The amount of each component administered according to the present method may, but does not have to be therapeutically effective by itself. That is, this invention specifically contemplates combinations wherein the amount of Compound I, or a pharmaceutically-acceptable salt thereof, and/or the amount of EGFR inhibitor, in the combination may be less than the amount that is therapeutically-effective for each active agent when said agent is administered in monotherapy.

Compound I, or a pharmaceutically acceptable salt thereof, may, for example, be administered orally. Erlotinib, or a pharmaceutically acceptable salt thereof, may, for example, be administered orally. Cetuximab may, for example, be administered intraperitoneally or intravenously.

The first component and the second component of the present invention are administered in any amount and for any duration that the combined amounts thereof are therapeutically effective in treating a proliferative disorder.

In embodiments of the present invention, Compound I, or a pharmaceutically acceptable salt thereof, is administered at a dosage amount of from about 200 mg/day to about 3000 mg/day, from about 1000 mg/day to about 2500 mg/day, or from about 1700 mg/day to about 2100 mg/day. In yet another embodiment, the dosage amount is about 1920 mg/day.

In an embodiment of the present invention, the foregoing amounts of Compound I, or a pharmaceutically acceptable salt thereof, may be administered as a single dose daily or divided, for example into equal doses (though this is not required), and administered twice daily (bid). For example, Compound I, or a pharmaceutically acceptable salt thereof, may be administered in a dosage amount of from about 100 mg to about 1500 mg bid, from about 500 mg to about 1250 mg bid, from about 850 mg to about 1050 mg bid, or about 960 mg bid.

In an embodiment of the present invention, the administration of Compound I, or a pharmaceutically acceptable salt thereof, occurs until disease progression or unacceptable toxicity.

In embodiments of the present invention, erlotinib, or a pharmaceutically acceptable salt thereof, is administered at a dosage amount of from about 20 mg/day to about 500 mg/day, from about 100 mg/day to about 400 mg/day, or from about 100 mg/day to about 200 mg/day.

In an embodiment of the present invention, the administration of erlotinib, or a pharmaceutically acceptable salt thereof, occurs until disease progression or unacceptable toxicity.

In an embodiment of the present invention, cetuximab is administered at a dosage amount of from about 50 mg/m$^2$/week to about 700 mg/m$^2$/week, from about 100 mg/m$^2$/week to about 600 mg/m$^2$/week, or from about 200 mg/m$^2$/week to about 500 mg/m$^2$/week.

In an embodiment, cetuximab is administered weekly with the first administration being in an amount of from about 400 mg/m² to about 500 mg/m² and each subsequent administration being in an amount of from about 200 mg/m² to about 300 mg/m².

In an embodiment, cetuximab is administered weekly with the first administration being in an amount of about 450 mg/m² and each subsequent administration being in an amount of about 250 mg/m².

In an embodiment of the present invention, the administration of cetuximab occurs until disease progression or unacceptable toxicity.

The present invention provides a method of treating a patient suffering from a proliferative disorder, comprising administering to the patient: (A) a first component which comprises, as an active agent, Compound I, or a pharmaceutically-acceptable salt thereof, in an amount of from about 200 mg/day to about 3000 mg/day, from about 1000 mg/day to about 2500 mg/day, from about 1700 mg/day to about 2100 mg/day or about 1920 mg/day; and (B) a second component which comprises, as an active agent, erlotinib, or a pharmaceutically acceptable salt thereof, in an amount of from about 20 mg/day to about 500 mg/day, from about 100 mg/day to about 400 mg/day, or from about 100 mg/day to about 200 mg/day. In embodiments of this invention, Compound I, or a pharmaceutically acceptable salt thereof, is administered twice daily. In an embodiment of this invention, the proliferative disorder is a solid tumor, in particular the disorder is selected from the group consisting of: colorectal cancer, melanoma, and thyroid cancer. In another embodiment of this invention, the proliferative disorder involves a tumor comprising b-Raf having the V600E mutation. In a particular embodiment of this invention, the proliferative disorder is colorectal cancer involving a tumor comprising b-Raf having the V600E mutation.

In an embodiment of the present invention, Compound I, or a pharmaceutically acceptable salt thereof, is administered orally in a dosage amount of from about 850 mg to about 1050 mg twice daily or about 960 mg twice daily, and erlotinib, or a pharmaceutically acceptable salt thereof, is administered orally in a dosage amount of from about 100 mg/day to about 400 mg/day, or from about 100 mg/day to about 200 mg/day. Both agents may, for example, be administered until disease progression or unacceptable toxicity.

The present invention also provides a method of treating a patient suffering from a proliferative disorder, comprising administering to the patient: (A) a first component which comprises, as an active agent, Compound I, or a pharmaceutically-acceptable salt thereof, in an amount of from about 200 mg/day to about 3000 mg/day, from about 1000 mg/day to about 2500 mg/day, from about 1700 mg/day to about 2100 mg/day or about 1920 mg/day; and (B) a second component which comprises, as an active agent, cetuximab in an amount of from about 50 mg/m²/week to about 700 mg/m²/week, from about 100 mg/m²/week to about 600 mg/m²/week, or from about 200 mg/m²/week to about 500 mg/m²/week. In an embodiment of this invention, the proliferative disorder is a solid tumor, in particular the disorder is selected from the group consisting of: colorectal cancer, melanoma, and thyroid cancer. In another embodiment of this invention, the proliferative disorder involves a tumor comprising b-Raf having the V600E mutation. In a particular embodiment of this invention, the proliferative disorder is colorectal cancer involving a tumor comprising b-Raf having the V600E mutation.

In an embodiment of the present invention, Compound I, or a pharmaceutically acceptable salt thereof, is administered orally in a dosage amount of from about 850 mg to about 1050 mg twice daily or about 960 mg twice daily, and cetuximab is administered intravenously in a dosage amount of from about 200 m g/m²/week to about 500 mg/m²/week. In an embodiment, cetuximab is administered initially as a 400 mg/m² dose as a 120-minute intravenous infusion, followed after a week by 250 mg/m² doses intravenously infused over 60 minutes once weekly. Both agents may, for example, be administered until disease progression or unacceptable toxicity.

The present invention also further provides a kit or a composition comprising: (A) a first component which comprises, as an active agent, Compound I, or a pharmaceutically-acceptable salt thereof and (B) a second component which comprises, as an active agent, erlotinib, or a pharmaceutically-acceptable salt or produg thereof.

The present invention also further provides a kit or a composition comprising: (A) a first component which comprises, as an active agent, Compound I, or a pharmaceutically-acceptable salt thereof and (B) a second component which comprises, as an active agent, cetuximab.

In another aspect of this invention, the components herein described above are administered in conjunction with radiotherapy and/or in conjunction with the administration of another active agent.

In an embodiment of the present invention, the components herein described above are administered together with a third component which comprises, as an active agent, a topoisomerase inhibitor. As previously stated, the amount of each component administered according to the present method may, but does not have to be therapeutically effective by itself and this invention specifically contemplates combinations wherein the amount of each of the active agents in the combination may be less than the amount that is therapeutically-effective for each active agent when said agent is administered in monotherapy.

In an embodiment of the present invention, the topoisomerase inhibitor is an inhibitor of type I topoisomerase. In an embodiment of the invention, the topoisomerase inhibitor is irinotecan, or a pharmaceutically acceptable salt thereof, for example, irinotecan hydrochloride (irinotecan HCl). Irinotecan HCl is sold as Camptosar® by Pfizer Inc., New York, U.S.A. Irinotecan, or the pharmaceutically acceptable salt thereof, may, for example, be administered intraperitoneally or intravenously.

In an embodiment of the present invention, irinotecan, or a pharmaceutically acceptable salt thereof, is administered at a dosage amount of from about 1 to about 400 mg/m²/week, or from about 1 to about 250 mg/m²/week. In another embodiment, irinotecan, or a pharmaceutically acceptable salt thereof, is administered at a dosage amount of from about 50 to about 200 mg/m²/week. In yet another embodiment, irinotecan, or a pharmaceutically acceptable salt thereof, is administered at a dosage amount of about 125 mg/m²/week.

In another embodiment, dosing of irinotecan, or a pharmaceutically acceptable salt thereof, is with a six week cycle at about 75 to about 175 mg/m² weekly, for example about 125 mg/m² weekly, for the first four weeks, for example on days 1, 8, 15, and 22. In another embodiment, dosing is with a six week cycle at about 130 to about 230 mg/m² weekly, for example about 180 mg/m² weekly, every two weeks starting on the first week, for example on days 1, 15, and 29. In a further embodiment, dosing is a once every three weeks at about from 300 to about 400 mg/m², for example about 350 mg/m². In yet another embodiment, dosing is a once every two weeks at about 130 to about 230 mg/m², for example about 180 mg/m². Dosing may be by infusion, for example, over about 90 minutes. Treatment may be until disease progression or unacceptable toxicity.

The dosage levels of each of the components may be modified by the physician to be lower or higher than that stated herein depending on the needs of the patient, and the reaction of the patient to the treatment. The dosages may be administered according to any dosage schedule determined by the physician in accordance with the requirements of the patient. For example, the dosages of each of the components may be administered in single or in divided doses over a period of several days, or alternating daily schedules.

The present invention also provides a method of treating a patient suffering from a proliferative disorder, comprising administering to the patient: (A) a first component which comprises, as an active agent, Compound I, or a pharmaceutically-acceptable salt thereof, in an amount of from about 200 mg/day to about 3000 mg/day, from about 1000 mg/day to about 2500 mg/day, from about 1700 mg/day to about 2100 mg/day or about 1920 mg/day; (B) a second component which comprises, as an active agent, cetuximab in an amount of from about 50 mg/m$^2$/week to about 700 mg/m$^2$/week, from about 100 mg/m$^2$/week to about 600 mg/m$^2$/week, or from about 200 mg/m$^2$/week to about 500 mg/m$^2$/week; and (C) a third component which comprises, as an active agent, irinotecan, or a pharmaceutically-acceptable salt thereof, in an amount of from about 1 to about 250 mg/m$^2$/week, about 50 to about 200 mg/m$^2$/week, or about 125 mg/m$^2$/week. In an embodiment of this invention, the proliferative disorder is a solid tumor, in particular the disorder is selected from the group consisting of: colorectal cancer, melanoma, and thyroid cancer. In another embodiment of this invention, the proliferative disorder involves a tumor comprising b-Raf having the V600E mutation. In a particular embodiment of this invention, the proliferative disorder is colorectal cancer involving a tumor comprising b-Raf having the V600E mutation.

In an embodiment of the present invention, Compound I, or a pharmaceutically acceptable salt thereof, is administered orally in a dosage amount of from about 850 mg to about 1050 mg twice daily or about 960 mg twice daily, cetuximab is administered intravenously in a dosage amount of from about 200 mg/m$^2$/week to about 500 mg/m$^2$/week, and irinotecan is administered intravenously in a dosage amount of from about 50 to about 200 mg/m$^2$/week, or about 125 mg/m$^2$/week. All agents may, for example, be administered until disease progression or unacceptable toxicity.

The present invention also further provides a kit or a composition comprising: (A) a first component which comprises, as an active agent, Compound I, or a pharmaceutically-acceptable salt thereof; (B) a second component which comprises, as an active agent, cetuximab; and (C) a third component which comprises, as an active agent, irinotecan, or a pharmaceutically-acceptable salt thereof.

Compound I exists in its natural state in a crystalline form. However, the amorphous form of the compound has greater solubility in water as compared with the crystalline form and thus has an improved dissolution rate and, therefore, improved bioavailability as compared to the crystalline form. As such, the amorphous form of the compound is preferred. Accordingly, in preferred embodiments of the method and kit of the present invention, Compound I is in substantially amorphous form and, more preferably, in amorphous form. As used herein, the term "substantially amorphous" material embraces material which has no more than about 10% crystallinity; and "amorphous" material embraces material which has no more than about 2% crystallinity.

In an embodiment of the present invention, Compound I is contained in a solid molecular complex formed with hydroxypropyl methyl cellulose acetate succinate (HPMC-AS). As used herein, the term "solid molecular complex" means a composition wherein Compound I is randomly distributed ("molecularly dispersed") within a matrix formed by HPMC-AS. In certain embodiments Compound I is present in the polymer in a final state of subdivision. In certain embodiments, Compound I is molecularly dispersed within the HPMC-AS matrix such that it is immobilized in its amorphous form. By "immobilized", it is meant that the molecules of Compound I interact with molecules of HPMC-AS in such a way that they are held in the aforementioned matrix and prevented from crystal nucleation due to lack of mobility. In some embodiments the polymer may prevent intramolecular hydrogen bonding or weak dispersion forces between two or more molecules of Compound I.

In some embodiments the ratio of the amount by weight of Compound I within the solid molecular complex to the amount by weight of HPMC-AS therein is from about 1:9 to about 5:5. In an embodiment, said ratio is from about 2:8 to about 4:6. In another embodiment, said ratio is about 3:7.

In certain embodiments of the method and kit of the present invention, the first component comprises the aforementioned solid molecular complex of Compound I and HPMC-AS blended with colloidal silicon dioxide. In certain embodiments, the blend is at least 0.5% by weight silicon dioxide. In an embodiment of the present invention, the blend is about 97% complex and about 3% silicon dioxide.

In another embodiment, the first component includes a composition comprising the aforementioned solid molecular complex, either blended or not blended with silicon dioxide as described above, and a pharmaceutically acceptable carrier. In certain embodiments, the aforementioned complex or blend comprising the same is suspended in the carrier. An example of a carrier is hydroxypropylcellulose (HPC). In an embodiment, the vehicle contains about 2% by weight HPC.

Each component may also contain additional agents such as preserving agents, solubilizing agents, stabilizing agents, wetting agents, emulsifying agents, sweetening agents, coloring agents, flavoring agents, salts for varying the osmotic pressure, buffers, coating agents and antioxidants.

In certain embodiments, the first component may comprise a solid molecular complex of Compound I and HPMC-AS blended with colloidal silicon dioxide, hydroxypropylcellulose, Crospovidone (a disintegrating agent), magnesium stearate (a lubricant that may be used in tablet and capsulation operations), and/or croscarmellose sodium (a disintegrating agent).

In an embodiment, the first component is a hard gelatin capsule comprising a solid molecular complex of Compound I and HPMC-AS blended with colloidal silicon dioxide, hydroxypropylcellulose, magnesium stearate, and croscarmellose sodium.

In an embodiment, the first component is a tablet comprising Compound I, or a pharmaceutically acceptable salt thereof. In an embodiment, the tablet comprises a solid molecular complex of Compound I, or a pharmaceutically acceptable salt thereof, and HPMC-AS. The complex may, for example, be blended with colloidal silicon dioxide, hydroxypropylcellulose, magnesium stearate, and croscarmellose sodium. The tablet may, for example, be coated with a film coating. The film coating may, for example, comprise polyvinyl alcohol, titanium dioxide, polyethylene glycol 3350, talc, and iron oxide red.

In certain embodiments, the second component may comprise cetuximab in solution. In an embodiment, the solution is about 2 mg/ml cetuximab.

In certain embodiments, the second component may comprise a tablet comprising erlotinib, or a pharmaceutically-acceptable salt thereof, for example erlotinib hydrochloride.

In certain embodiments, the third component may comprise a solution comprising irinotecan, or a pharmaceutically acceptable salt thereof, for example irinotecan hydrochloride. In an embodiment, the solution is an about 5% dextrose solution. In an embodiment, each ml of the solution contains about 20 mg irinotecan hydrochloride, about 45 mg sorbitol, and about 0.9 mg lactic acid. In an embodiment, the solution has a pH of from about 3.0 to about 3.8, for example, about 3.5.

In addition, the present invention provides the use of Compound I, or a pharmaceutically-acceptable salt thereof, and an EGFR inhibitor for the treatment of a proliferative disorder.

The invention further provides the use of Compound I, or a pharmaceutically-acceptable salt thereof, and an EGFR inhibitor for the preparation of a medicament for the treatment of a proliferative disorder.

Applicants have conducted studies using mice containing a human colorectal cancer xenograft. Applicants found that the combination of Compound I at 75 mg/kg bid and erlotinib hydrochloride at 67 mg/kg qd produced tumor growth inhibition (TGI) and increased life span (ILS) results that were significantly better than correlative monotherapy results at p<0.05 as well as results achieved with erlotinib hydrochloride monotherapy at 100 mg/kg qd. In addition, 9 out of the 10 mice subjected to the combination therapy had partial regressions whereas no regressions (partial or complete) were observed with any of the monotherapy groups. These studies indicate that treating patients with a combination of Compound I and erlotinib hydrochloride is superior to treatment with either agent alone. Further, they indicate that combining the two agents allows for at least reduction in the dose of erlotinib hydrochloride to obtain equivalent or better results.

Applicants also found that the combination of Compound I at 25 mg/kg bid and cetuximab at 40 mg/kg 2×/wk growth inhibition (TGI) and increased life span (ILS) results that were significantly better than correlative monotherapy results at p<0.05 and also better than the results achieved with monotherapy of Compound I at 75 mg/kg bid. Applicants also found that both the combination of Compound I at 75 mg/kg bid and cetuximab at 40 mg/kg 2×/wk produced TGI and ILS results that were significantly better than correlative monotherapy results at p<0.05 and also better than the results achieved with monotherapy of Compound I at 25 mg/kg bid. In addition, 7 out of the 9 mice subjected to the Compound I at 25 mg/kg bid and cetuximab at 40 mg/kg 2×/wk combination therapy had partial regressions and 10 out of 10 mice subjected to the Compound I at 75 mg/kg bid and cetuximab at 40 mg/kg 2×/wk combination therapy exhibited regression with 7 being partial and 3 being complete. By contrast, no regressions (partial or complete) were observed with any of the monotherapy groups.

In addition to the above, applicants found that the combination of Compound I at 25 mg/kg bid, cetuximab at 40 mg/kg 2×/wk, and irinotecan hydrochloride at 40 mg/kg q4d×5 produced tumor growth inhibition (TGI) and increased life span (ILS) results that were significantly better than correlative monotherapy results at p<0.05 and also better than the results achieved with Compound I at 25 mg/kg bid and irinotecan hydrochloride at 40 mg/kg q4d×5 combination therapy and Compound I at 25 mg/kg bid and cetuximab at 40 mg/kg 2×/wk combination therapy. In the study, the Compound I at 25 mg/kg bid and irinotecan hydrochloride at 40 mg/kg q4d×5 combination therapy resulted in 4 out of 10 partial regressions and no complete regressions and the Compound I at 25 mg/kg bid and cetuximab at 40 mg/kg 2×/wk combination therapy resulted in 5 out of 10 partial regressions and no complete regressions. The cetuximab at 40 mg/kg 2×/wk and irinotecan at 40 mg/kg q4d×5 combination therapy and the correlative Compound I, cetuximab, and irinotecan hydrochloride monotherapies resulted in no regressions. By contrast, the Compound I at 25 mg/kg bid, cetuximab at 40 mg/kg 2×/wk, and irinotecan hydrochloride at 40 mg/kg q4d×5 therapy produced 10 out of 10 regressions with 9 being partial and one being complete.

These studies indicate that treating patients with a combination of Compound I and cetuximab is superior to treatment with either agent alone. Further, they indicate that combining the two agents allows for at least reduction in the dose of Compound I to obtain equivalent or better results. In addition, the studies indicate that treating patients with a combination of Compound I, cetuximab, and irinotecan hydrochloride produces even more superior results.

EXAMPLES

The invention will be more fully understood by reference to the following examples. They should not, however, be construed as limiting the scope of the invention.

Abbreviations used herein are as follows:
q.s. as much as needed
× times
po orally
ip intraperitoneally
bid twice daily
wk week
qd once daily
q4d×5 once every four days for a total of five doses
BWL body weight loss In the examples below, weight loss was graphically represented as percent change in mean group body weight, using the formula: $((W-W_0)/W_0) \times 100$, where 'W' represents mean body weight of the treated group at a particular day, and '$W_0$' represents mean body weight of the same treated group at initiation of treatment. Maximum weight loss was also represented using the above formula, and indicated the maximum percent body weight loss that was observed at any time during the entire experiment for a particular group.

Efficacy data was graphically represented as the mean tumor volume±standard error of the mean (SEM). In addition, tumor volumes of treated groups were presented as percentages of tumor volumes of the control groups (% T/C), using the formula: $100 \times ((T-T_0)/(C-C_0))$, where T represented mean tumor volume of a treated group on a specific day during the experiment, $T_0$ represented mean tumor volume of the same treated group on the first day of treatment; C represented mean tumor volume of a control group on the specific day during the experiment, and $C_0$ represented mean tumor volume of the same treated group on the first day of treatment.

Tumor volume (in cubic millimeters) was calculated using the ellipsoid formula: $(D \times (d^2))/2$, where "D" represents the large diameter of the tumor and "d" represents the small diameter.

Also, tumor regression and/or percent change in tumor volume was calculated using the formula: $((T-T_0)/T_0) \times 100$, where 'T' represents mean tumor volume of the treated group at a particular day, and '$T_0$' represents mean tumor volume of the same treated group at initiation of treatment.

Statistical analysis was determined by the rank sum test and One Way Anova and a post-hoc Bonferroni t-test (SigmaStat, version 2.0, Jandel Scientific, San Francisco, Calif., USA). Differences between groups were considered to be significant when the probability value (p) was ≤0.05.

For survival assessment, the percent of increased life space (ILS) was calculated as: 100×[(median survival day of treated group−median survival day of control group)/median survival day of control group]. Median survival was determined utilizing Kaplan Meier survival analysis. Survival in treated groups was statistically compared with the vehicle group and survival comparisons were done between groups using the log-rank test (Graph Pad Prism, La Jolla, Calif., USA). Differences between groups were considered significant when the probability value (p) was ≤0.05.

Example 1

This example describes the formation of a suspension comprising Compound I.

A solid molecular complex comprising Compound I and hydroxypropyl methyl cellulose acetate succinate (HPMC-AS) was first formed.

Compound I and HPMC-AS in a ratio of approximately 3:7, respectively, were dissolved in dimethylacetamide (DMA). The resulting solution was then added with stirring to very cold dilute hydrochloric acid resulting in the co-precipitation of Compound I and HPMC-AS as a solid molecular complex wherein Compound I was present in a nanoparticulate size range. The ratio of DMA to acid was in the range of 1:5 to 1:10.

The co-precipitate was then washed with water to remove DMA, filtered, dried to <2% moisture content and passed through a #30 mesh screen prior to evaluation. The resulting solid molecular complex was 30% by weight Compound I and 70% by weight HPMC.

The complex was then blended with colloidal silicon dioxide (available as Aerosil® 200 from Evonik Industries AG, Essen, Germany) such that, per 100 g of the blend, 97 g was the complex and 3 g was colloidal silicon dioxide.

An aqueous vehicle containing 2% hydroxypropylcellulose (available as Klucel LF from Aqualon, Wilmington, Del., USA) and 1N HCl at Qs to pH4 for the purpose of pH adjustment was then prepared.

23.2 ml of the vehicle was equilibrated to room temperature and slowly transferred into 773.2 mg of the aforementioned blend. The resulting preparation was then slowly mixed until a homogenous suspension was obtained. The resulting suspension contained 9.375 mg/ml of Compound I.

The suspension was stored at 2-8° C. and protected from light.

Example 2

Mice were Implanted with Human HT-29 Cell Xenografts. The Mice, Cell Line Used, and Implantation are Described Below Female athymic Crl:NU-Foxn1nu mice were used for efficacy testing (Charles River, Wilmington, Mass., USA). Mice were 10-12 weeks of age and weighed 23-25 grams. The health of the mice was assessed daily by observation and analysis of blood samples taken from sentinel animals on shared shelf racks. All animals were allowed to acclimate and recover from shipping-related stress for one week. Autoclaved water and irradiated food (5058-ms Pico Lab mouse chow, Purina Mills, Richmond, Ind., USA) were provided ad libitum, and the animals were kept in a 12 hour light and dark cycle. Cages, bedding and water bottles were autoclaved before use and changed weekly. All animal experiments were conducted in accordance with the Guide for the Care and Use of Laboratory Animals, local regulations, and protocols approved by the Roche Animal Care and Use Committee in our AAALAC accredited facility.

HT-29 cells (American Type Culture Collection, Rockville, Md.) were grown in McCoy-5 medium supplemented with 10% Fetal Bovine Serum (FBS) and 1% of 200 nM L-glutamine, scaled up, harvested, and prepared so that each mouse received $3\times10^6$ cells in 0.2 ml calcium and magnesium free phosphate-buffered saline (PBS). Cells were implanted subcutaneously in the right flank of each of the mice.

Example 3

This example describes the preparation of a suspension of erlotinib hydrochloride.

One gram of Tween 80 was added to approximately 950 ml of water. While stirring at high speed, three grams of sodium carboxymethyl cellulose were added to the solution. Mixing was continued until the sodium carboxymethyl cellulose was dissolved. Water was then added q.s. until 1 liter. 12.5 grams of erlotinib hydrochloride (available from Genentech as Tarceva®) was then suspended in the solution and passed through a dissolver. The solution was then deaereated with nitrogen.

The contents of the final suspension are as follows.

| Component | Amount |
| --- | --- |
| Erlotinib hydrochloride | 12.5 g |
| Sodium carboxymethyl cellulose | 3 g |
| Tween 80 | 1 g |
| Water for injection | q.s. to 1 liter |

This provided a solution that was 12.5 mg/ml erlotinib hydrochloride.

The solution was stored at 2 to 8° C.

Example 4

A suspension comprising Compound I was produced as described in Example 1.

The 12.5 mg/ml erlotinib hydrochloride solution was made as described in Example 3. A further 8.30 mg/ml solution was made in a manner similar to that in example 3 with the exception that 8.30 g of erlotinib hydrochloride was used instead of 12.5 g.

HT-29 xenograft-containing mice as produced in the manner described in Example 2 were randomized into groups of 10 mice each according to tumor volume so that all groups had similar starting mean tumor volumes. The approximate starting mean tumor volume for this study was 136 mm³.

Treatment of the mice began on day 12 post-cell implant and ended at day 29 post cell implant. Each group was subjected to a different therapy as follows:
(1) mice receiving Compound I vehicle bid po and erlotinib hydrochloride vehicle qd po;
(2) mice receiving Compound I at 75 mg/kg bid po;
(3) mice receiving erlotinib hydrochloride at 67 mg/kg qd po;
(4) mice receiving erlotinib hydrochloride at 100 mg/kg qd po;
(5) mice receiving Compound I at 75 mg/kg bid po and erlotinib hydrochloride at 67 mg/kg qd po.

The Compound I suspension and its corresponding vehicle were dosed using a sterile 1 cc syringe and 18-gauge gavage needle (0.2 ml/animal) twice daily. The erlotinib hydrochloride solution and its corresponding vehicle were dosed using a sterile 1 cc syringe and 18-gauge needle (0.2 ml/animal) once daily starting on day 12 and ending on day 29 post-implantation. The 12.5 mg/ml solution was used for the erlotinib hydrochloride at 100 mg/kg groups and the 8.30 mg/ml solution was used for the erlotinib hydrochloride at 67 mg/kg qd groups. All dosing was based on an average mouse weight of 25 grams.

Tumor measurements were taken once or twice per week. All animals were individually followed throughout the experiment.

Figure 2:
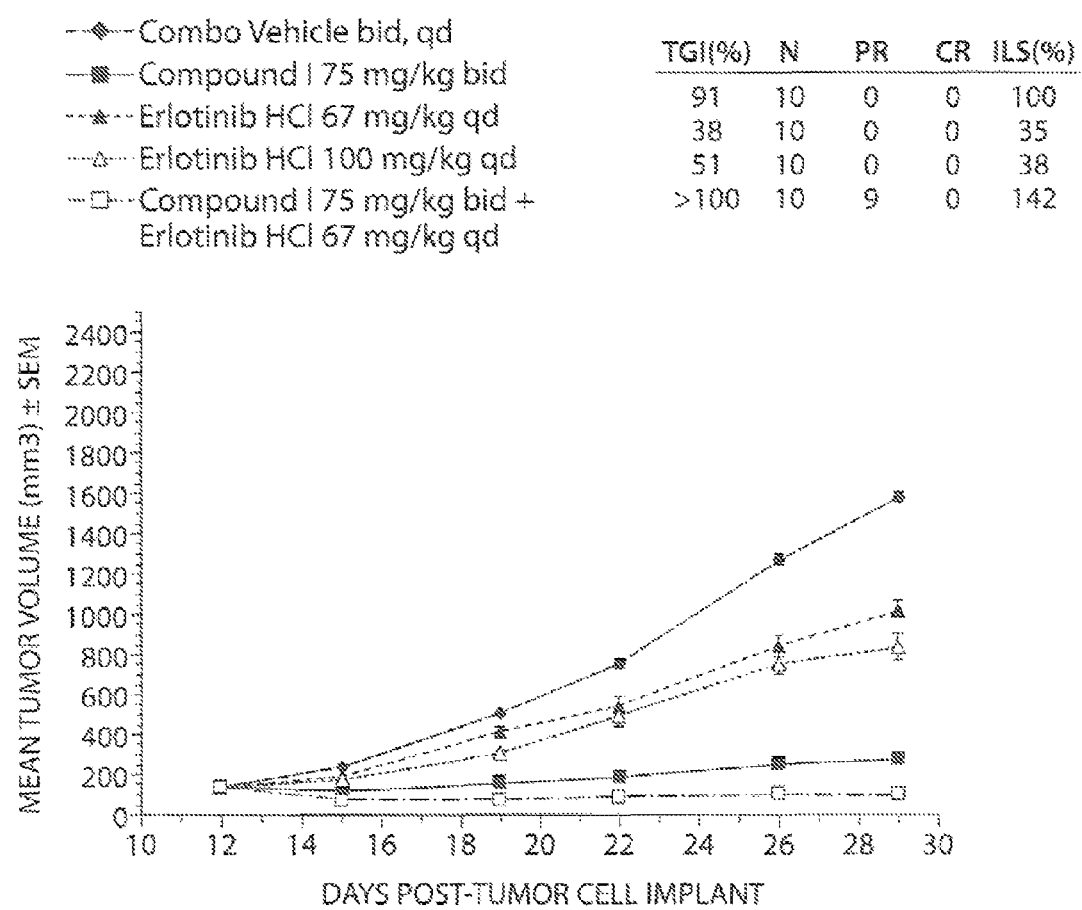
FIG. 2 illustrates the antitumor activity, as demonstrated by the change in mean tumor volume over time, of Compound I monotherapy at 75 mg/kg bid, erlotinib hydrochloride monotherapy at 67 mg/kg qd, erlotinib hydrochloride monotherapy at 100 mg/kg qd, and Compound I at 75 mg/kg bid and erlotinib hydrochloride at 67 mg/kg qd combination therapy.

Toxicity with any of the aforementioned groups. The group receiving combination therapy of Compound I at 75 mg/kg bid and erlotinib hydrochloride at 67 mg/kg qd exhibited greater than 100% TGI with 9 out of 10 partial regressions (PRs). See Tables 2 and 3 and FIG. 2.

TABLE 2

| Group | Frequency | Route | Mean Tumor Volume (mm$^3$) Start Study | SEM | SD | Mean Tumor Volume (mm$^3$) End Study | SD | SEM |
|---|---|---|---|---|---|---|---|---|
| Combo Vehicle | bid, qd | po | 137.99 | ±1.81 | ±5.74 | 1580.20 | ±74.00 | ±23.40 |
| Compound I 75 mg/kg | bid | po | 134.27 | ±2.11 | ±6.67 | 270.24 | ±68.06 | ±21.52 |
| Erlotinib HCl 67 mg/kg | qd | po | 136.46 | ±2.69 | ±8.49 | 1025.10 | ±142.96 | ±45.21 |
| Erlotinib HCl 100 mg/kg | qd | po | 133.82 | ±3.09 | ±9.76 | 838.75 | ±215.21 | ±68.06 |
| Compound I 75 mg/kg + Erlotinib HCl 67 mg/kg | bid, qd | po | 137.16 | ±2.08 | ±6.59 | 102.14 | ±21.26 | ±6.72 |

In general, no major signs of toxicity were noted in any dose group in this study described as assessed by measuring changes in body weight and gross observation of individual animals. Erlotinib hydrochloride at 100 mg/kg qd is historically not well tolerated in combination (Higgins et al., *Anti-cancer Drugs*, 15:503-12 (2004)), hence use of 67 mg/kg qd for the combination arm to ensure tolerability. Erlotinib hydrochloride at 100 mg/kg qd was included as a monotherapy arm for comparison. Compound I however is very well tolerated and was dosed at 75 mg/kg bid even in combination with erlotinib hydrochloride. EGFR inhibitor related skin rash was common in mice treated with erlotinib hydrochloride with a self limiting nature, even under continuous treatment. See Table 1 and FIG. 1.

TABLE 1

| Group | Frequency | Route | % Change in Body Weight at end of Study Day 29 | Max % Weight Loss | Max % # animals ≥ 20% BWL | Mortality |
|---|---|---|---|---|---|---|
| Combo Vehicle | bid, qd | po | 3.5 | -1.7 | 4.4 | 0 | 0 |
| Compound I 75 mg/kg | bid | po | 2.4 | -0.1 | 3.6 | 0 | 0 |
| Erlotinib HCl 67 mg/kg | qd | po | 1.7 | -1.0 | 2.5 | 0 | 0 |
| Erlotinib HCl 100 mg/kg | qd | po | 2.9 | -1.6 | 3.0 | 0 | 0 |
| Compound I 75 mg/kg + Erlotinib HCl 67 mg/kg | bid, qd | po | 2.5 | -1.0 | 2.5 | 0 | 0 |

Tumor Growth Inhibition (TGI)

The group receiving Compound I monotherapy at 75 mg/kg bid exhibited 91% TGI whereas the group receiving erlotinib hydrochloride at 100 mg/kg qd exhibited 51% TGI and the group receiving erlotinib hydrochloride at 67 mg/kg qd exhibited 38% TGI. No tumor regression was observed

TABLE 3

| Group | % T/C end of study Day: 29 | % Inhibition end of study Day: 29 | P Value End of study Day: 29 | Average % Regression per Group | Partial Regression | Complete Regression | Animals per Group | % Tumor Growth Inhibition |
|---|---|---|---|---|---|---|---|---|
| Combo Vehicle | — | — | — | — | 0 | 0 | 10 | — |
| Compound I 75 mg/kg bid | 9 | 91 | <0.001 | — | 0 | 0 | 10 | 91 |
| Erlotinib HCl 67 mg/kg qd | 62 | 38 | <0.001 | — | 0 | 0 | 10 | 38 |

TABLE 3-continued

| Group | % T/C end of study Day: 29 | % Inhibition end of study Day: 29 | P Value End of study Day: 29 | Average % Regression per Group | Partial Regression | Complete Regression | Animals per Group | % Tumor Growth Inhibition |
|---|---|---|---|---|---|---|---|---|
| Erlotinib HCl 100 mg/kg qd | 49 | 51 | <0.001 | — | 0 | 0 | 10 | 51 |
| Compound I 75 mg/kg bid + Erlotinib HCl 67 mg/kg qd | −2 | regression | <0.001 | 26 | 9 | 0 | 10 | >100 |

Assessment of Survival

Figure 3:
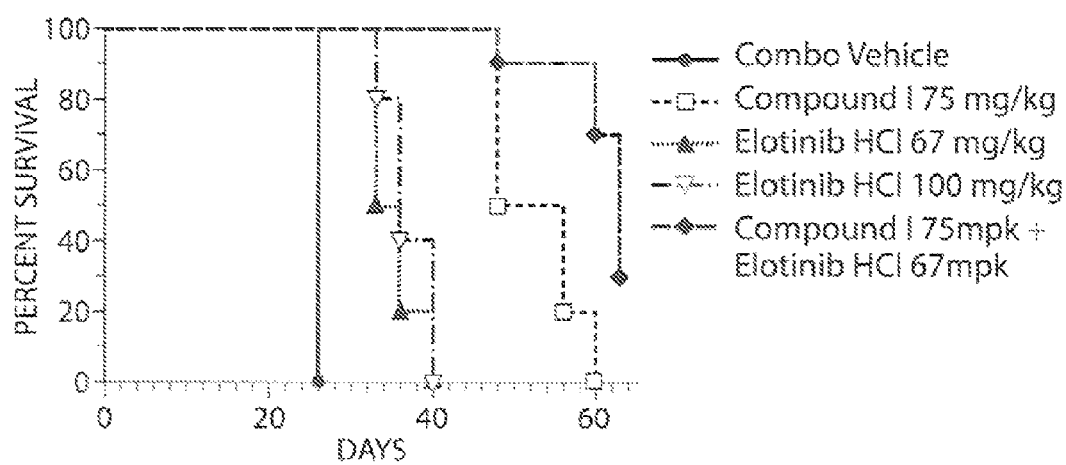
FIG. 3 illustrates the effect on survival, as demonstrated by percentage of surviving mice over time, of Compound I monotherapy at 75 mg/kg bid, erlotinib hydrochloride monotherapy at 67 mg/kg qd, erlotinib hydrochloride monotherapy at 100 mg/kg qd, and Compound I at 75 mg/kg bid and erlotinib hydrochloride at 67 mg/kg qd combination therapy.

The group receiving Compound I monotherapy at 75 mg/kg exhibited 100% increased life span (ILS). The group receiving erlotinib hydrochloride monotherapy at 100 mg/kg qd exhibited 38% ILS. The group receiving erlotinib hydrochloride monotherapy at 67 mg/kg qd exhibited 35% ILS. The group receiving combination therapy of Compound I at 75 mg/kg bid and erlotinib hydrochloride at 67 mg/kg qd exhibited 142% ILS. See Table 4 and FIG. 3.

TABLE 4

| | ILS Calculations | | | |
|---|---|---|---|---|
| Group | 50% Treatment Days | 50% Vehicle Days | % ILS | p value |
| Combo Vehicle | — | — | — | — |
| Compound I 75 mg/kg bid | 52 | 26 | 100 | <0.0001 |
| Erlotinib HCl 67 mg/kg qd | 35 | 26 | 35 | <0.0001 |
| Erlotinib HCl 100 mg/kg qd | 36 | 26 | 38 | <0.0001 |
| Compound I 75 mg/kg bid + Erlotinib HCl 67 mg/kg qd | 63 | 26 | 142 | <0.0001 |

Statistical Analysis

The % TGI in the Compound I at 75 mg/kg bid and erlotinib hydrochloride at 67 mg/kg qd combination therapy was statistically superior to that of all monotherapy arms (p<0.05). The % ILS in the Compound I at 75 mg/kg bid and erlotinib hydrochloride at 67 mg/kg qd combination therapy combination therapy group was also statistically superior to that of all monotherapy arms tested (p<0.05 for all comparisons). See Table 5.

TABLE 5

| Treatment | versus | Treatment | TGI p value* | ILS p value** |
|---|---|---|---|---|
| Compound I 75 mg/kg bid | | Erlotinib HCl 67 mg/kg qd | <0.05 | <0.0001 |
| Compound I 75 mg/kg bid | | Erlotinib HCl 100 mg/kg qd | <0.05 | <0.0001 |
| Compound I 75 mg/kg bid | | Erlotinib HCl 67 mg/kg qd + Compound I 75 mg/kg bid | <0.05 | 0.0003 |
| Erlotinib HCl 67 mg/kg qd | | Erlotinib HCl 100 mg/kg qd | <0.05 | 0.2041 |
| Erlotinib HCl 67 mg/kg qd | | Erlotinib HCl 67 mg/kg qd + Compound I 75 mg/kg bid | <0.05 | <0.0001 |
| Erlotinib HCl 100 mg/kg qd | | Erlotinib HCl 67 mg/kg qd + Compound I 75 mg/kg bid | <0.05 | <0.0001 |

*One-Way ANOVA, post-hoc Bonferroni
**Breslow-Gehan-Wilcoxon

Example 5

Two suspensions comprising Compound I were made in a manner similar to that in example 1 with the exception that 20 ml of a 9.375 mg/ml suspension was made using 19.4 ml of the vehicle and 644 mg of the blend and 20 ml of a 3.125 mg/ml suspension was made using 19.8 ml of the vehicle and 214.8 mg of the blend.

Cetuximab was purchased from ImClone Systems, Inc. (available as Erbitux®) as a 2 mg/ml solution.

HT-29 xenograft-containing mice as produced in the manner described in Example 2 were randomized into groups of 10 mice each according to tumor volume so that all groups had similar starting mean tumor volumes. The approximate starting mean tumor volume for this study was 135 mm$^3$.

Treatment began on day 12 post-cell implant and ended at day 34 post cell implant. Each group was subjected to a different therapy as follows:
(1) mice receiving Compound I vehicle bid po and cetuximab vehicle 2×/wk ip;
(2) mice receiving cetuximab at 40 mg/kg 2×/wk ip;
(3) mice receiving Compound I at 25 mg/kg bid po;
(4) mice receiving Compound I at 75 mg/kg bid po;
(5) mice receiving Compound I at 25 mg/kg bid po and cetuximab at 40 mg/kg 2×/wk ip;
(6) mice receiving Compound I at 75 mg/kg bid po and cetuximab at 40 mg/kg 2×/wk ip.

The Compound I suspension and its corresponding vehicle were dosed using a sterile 1 cc syringe and 18-gauge gavage needle (0.2 ml/animal) twice daily. The 9.375 mg/ml suspension was used for the Compound I at 75 mg/kg bid groups and the 3.125 mg/ml suspension was used for the Compound I at 25 mg/kg bid groups. Cetuximab and its corresponding vehicle were dosed intraperitoneally using a sterile 1 cc syringe and 26-gauge needle (0.5 ml/animal) twice a week on a Monday/Thursday or Tuesday/Friday schedule. All dosing was based on an average mouse weight of 25 grams.

Tumor measurements were taken once or twice per week. All animals were individually followed throughout the experiment.

Toxicity

Figure 4:
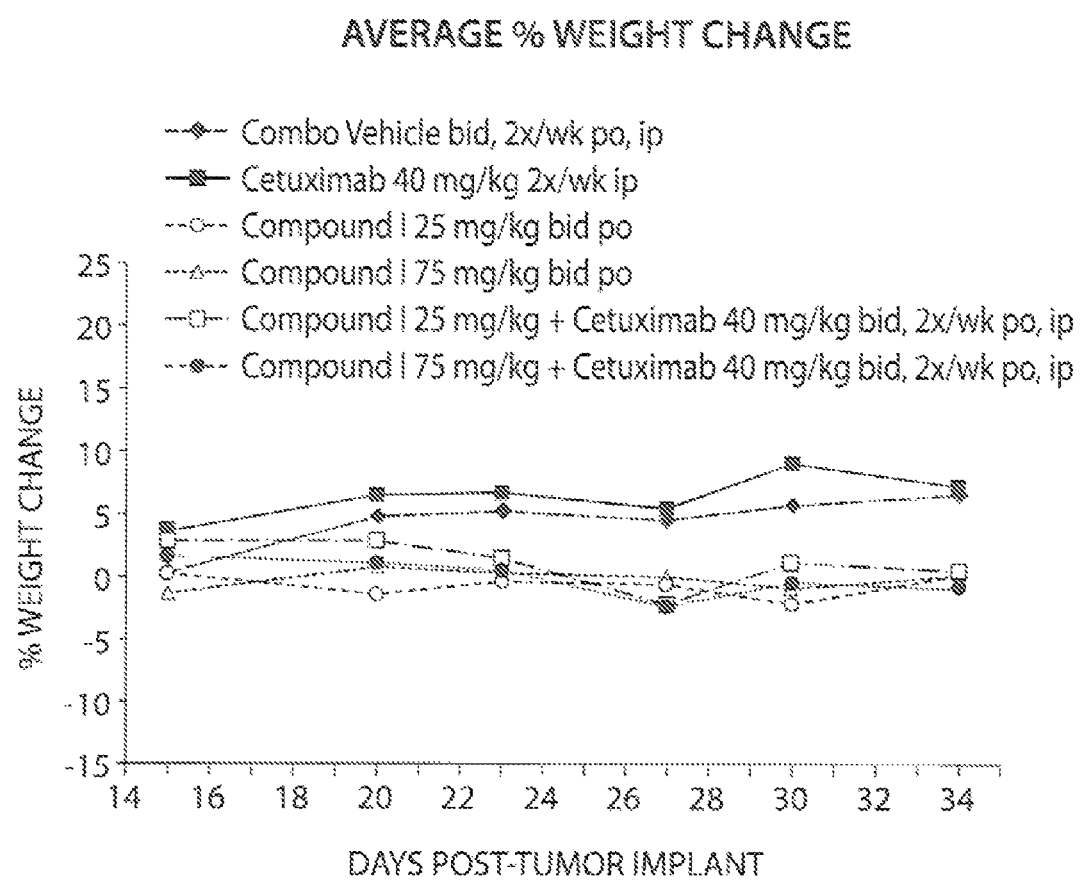
FIG. 4 illustrates the tolerability, as demonstrated by % body weight change, of Compound I monotherapy at 75 mg/kg bid, Compound I monotherapy at 25 mg/kg bid, cetuximab monotherapy at 40 mg/kg 2x/wk, Compound I at 25 mg/kg bid and cetuximab at 40 mg/kg 2x/wk combination therapy, and Compound I at 75 mg/kg bid and cetuximab at 40 mg/kg 2×/wk combination therapy.

In general, no major signs of toxicity were noted in any dose group in this study described as assessed by measuring changes in body weight and gross observation of individual animals. See Table 6 and FIG. 4. EGFR inhibitor related skin rash was common in cetuximab treated mice with a self-limiting nature even under continuous treatment. One mouse appeared to have a bacterial infection as a sequela to rash leading to progressive weight loss >20% thereby requiring humane sacrifice. This mouse was censored from the overall tumor growth inhibition and survival analysis.

pound I at 25 mg/kg bid and cetuximab at 40 mg/kg 2×/wk exhibited 7 out of 10 partial regressions (PRs) but no complete regressions (CRs). The group receiving Compound I at 75 mg/kg bid and cetuximab at 40 mg/kg 2×/wk exhibited 7 out of 10 PRs and 3 out of 10 CRs.

Figure 5:
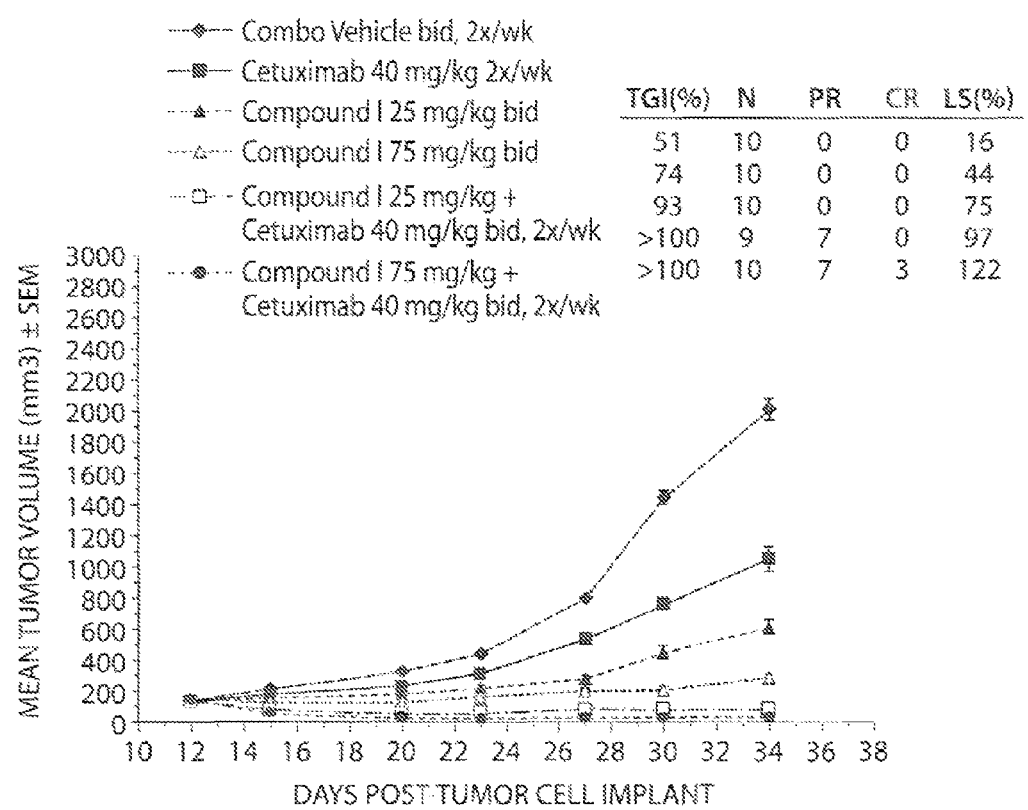
FIG. 5 illustrates the antitumor activity, as demonstrated by the change in mean tumor volume over time, of Compound I monotherapy at 75 mg/kg bid, Compound I monotherapy at 25 mg/kg bid, cetuximab monotherapy at 40 mg/kg 2×/wk, Compound I at 25 mg/kg bid and cetuximab at 40 mg/kg 2×/wk combination therapy, and Compound I at 75 mg/kg bid and cetuximab at 40 mg/kg 2×/wk combination therapy.

See Tables 7 and 8 and FIG. 5.

TABLE 6

| Group | Frequency | Route | % Change in Body Weight at end of Study Day 34 | Max % Weight Loss | Max % Weight Gain | # animals ≥ 20% BWL | Mortality |
|---|---|---|---|---|---|---|---|
| Combo Vehicle | bid, 2×/wk | po, ip | 6.6 | 0.5 | 6.6 | 0 | 0 |
| Cetuximab 40 mg/kg | 2×/wk | ip | 7.2 | 3.7 | 8.9 | 0 | 0 |
| Compound I 25 mg/kg | bid | po | 0.1 | −2.2 | 0.3 | 0 | 0 |
| Compound I 75 mg/kg | bid | po | −0.1 | −1.4 | 0.7 | 0 | 0 |
| Compound I 25 mg/kg + Cetuximab 40 mg/kg | bid, 2×/wk | po, ip | 0.5 | −2.1 | 2.9 | 1 | 0 |
| Compound I 25 mg/kg + Cetuximab 40 mg/kg | bid, 2×/wk | po, ip | −0.8 | −2.4 | 1.6 | 0 | 0 |

Tumor Growth Inhibition (TGI)

The group receiving Compound I monotherapy at 25 mg/kg bid exhibited 74% TGI and the group receiving Compound I monotherapy at 75 mg/kg bid exhibited 93% TGI. The group receiving cetuximab at 40 mg/kg 2×/wk achieved 51% TGI. No tumor regression was observed with any of the aforementioned groups. Both combination therapy groups, however, exhibited >100% TGI. The group receiving Com-

TABLE 7

| Group | Frequency | Route | Mean Tumor Volume (mm³) Start Study | SEM | SD | Mean Tumor Volume (mm³) End Study | SD | SEM |
|---|---|---|---|---|---|---|---|---|
| Combo Vehicle | bid, 2×/wk | po, ip | 133.95 | ±2.31 | ±7.31 | 2011.75 | ±227.22 | ±71.85 |
| Cetuximab 40 mg/kg | 2×/wk | ip | 133.13 | ±2.34 | ±7.39 | 1052.49 | ±249.18 | ±78.80 |
| Compound I 25 mg/kg | bid | po | 135.97 | ±2.75 | ±8.71 | 615.99 | ±148.01 | ±46.81 |
| Compound I 75 mg/kg | bid | po | 137.05 | ±2.35 | ±7.44 | 275.66 | ±56.34 | ±17.82 |
| Compound I 25 mg/kg + Cetuximab 40 mg/kg | bid, 2×/wk | po, ip | 134.56 | ±2.24 | ±7.07 | 90.98 | ±41.56 | ±13.85 |
| Compound I 75 mg/kg + Cetuximab 40 mg/kg | bid, 2×/wk | po, ip | 137.04 | ±3.20 | ±10.10 | 26.45 | ±20.60 | ±6.52 |

TABLE 8

| Group | % T/C end of study Day: 34 | % Inhibition end of study Day: 34 | p value End of study Day: 34 | Average % Regression per Group | Partial Regression | Complete Regression | Animals per Group | % Tumor Growth Inhibition |
|---|---|---|---|---|---|---|---|---|
| Combo Vehicle | — | — | — | — | 0 | 0 | 10 | — |
| Cetuximab 40 mg/kg 2x/wk | 49 | 51 | <0.001 | — | 0 | 0 | 10 | 51 |
| Compound I 25 mg/kg bid | 26 | 74 | <0.001 | — | 0 | 0 | 10 | 74 |
| Compound I 75 mg/kg bid | 7 | 93 | <0.001 | — | 0 | 0 | 10 | 93 |
| Compound I 25 mg/kg bid + Cetuximab 40 mg/kg 2x/wk | −2 | regression | <0.001 | 39 | 7 | 0 | 9 | >100 |
| Compound I 75 mg/kg bid + Cetuximab 40 mg/kg 2x/wk | −6 | regression | <0.001 | 81 | 7 | 3 | 10 | >100 |

Assessment of Survival

Figure 6:
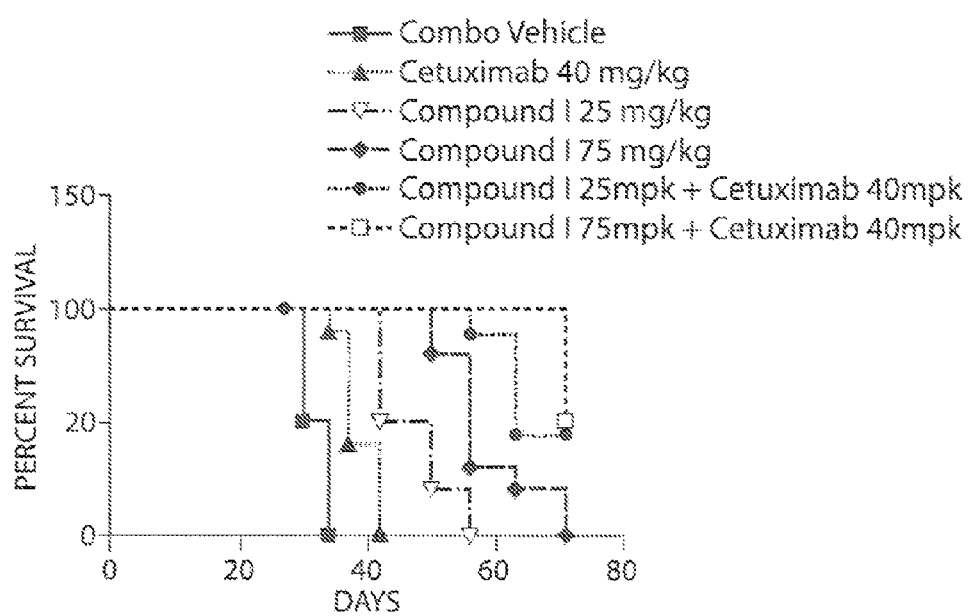
FIG. 6 illustrates the effect on survival, as demonstrated by percentage of surviving mice over time, of Compound I monotherapy at 75 mg/kg bid, Compound I monotherapy at 25 mg/kg bid, cetuximab monotherapy at 40 mg/kg 2×/wk, Compound I at 25 mg/kg bid and cetuximab at 40 mg/kg 2×/wk combination therapy, and Compound I at 75 mg/kg bid and cetuximab at 40 mg/kg 2×/wk combination therapy.

The group receiving Compound I monotherapy at 25 mg/kg bid exhibited 44% ILS and the group receiving Compound I monotherapy at 75 mg/kg bid exhibited 75% ILS. The group receiving cetuximab at 40 mg/kg 2x/wk achieved 16% ILS. The group receiving Compound I at 25 mg/kg bid and cetuximab at 40 mg/kg 2x/wk exhibited 97% ILS. The group receiving Compound I at 75 mg/kg bid and cetuximab at 40 mg/kg 2x/wk exhibited 122% ILS. See Table 9 and FIG. 6.

TABLE 9

| Group | ILS Calculations ||||
|---|---|---|---|---|
| | 50% Treatment Days | 50% Vehicle Days | % ILS | p value |
| Combo Vehicle | — | — | — | — |
| Cetuximab 40 mg/kg 2x/wk | 37 | 32 | 16 | <0.0001 |
| Compound I 25 mg/kg bid | 46 | 32 | 44 | <0.0001 |
| Compound I 75 mg/kg bid | 56 | 32 | 75 | <0.0001 |
| Compound I 25 mg/kg bid + Cetuximab 40 mg/kg 2x/wk | 63 | 32 | 97 | <0.0001 |
| Compound I 75 mg/kg bid + Cetuximab 40 mg/kg 2x/wk | 71 | 32 | 122 | <0.0001 |

Statistical Analysis

The % TGIs of both the Compound I at 25 mg/kg bid and cetuximab at 40 mg/kg 2x/wk combination therapy and the Compound I at 75 mg/kg bid and cetuximab at 40 mg/kg 2x/wk combination therapy were statistically superior to that of all monotherapy arms (p<0.05). The % ILSs achieved in both monotherapies were also statistically superior to that of all monotherapy arms tested (p<0.05 for all comparisons). See Table 10.

TABLE 10

| Treatment | versus | Treatment | TGI p value* | ILS p value** |
|---|---|---|---|---|
| Cetuximab 40 mg/kg 2x/wk | | Compound I 25 mg/kg bid | <0.05 | 0.0010 |
| Cetuximab 40 mg/kg 2x/wk | | Compound I 75 kg/mg bid | <0.05 | <0.0001 |
| Cetuximab 40 mg/kg 2x/wk | | Compound I 25 mg/kg bid + Cetuximab 40 mg/kg 2x/wk | <0.05 | <0.0001 |
| Cetuximab 40 mg/kg 2x/wk | | Compound I 75 kg/mg bid + Cetuximab 40 mg/kg 2x/wk | <0.05 | <0.0001 |
| Compound I 25 mg/kg bid | | Compound I 75 kg/mg bid | <0.05 | 0.0025 |
| Compound I 25 mg/kg bid | | Compound I 25 mg/kg bid + Cetuximab 40 mg/kg 2x/wk | <0.05 | <0.0001 |
| Compound I 25 mg/kg bid | | Compound I 75 mg/kg bid + Cetuximab 40 mg/kg 2x/wk | <0.05 | <0.0001 |
| Compound I 75 mg/kg bid | | Compound I 25 mg/kg bid + Cetuximab 40 mg/kg 2x/wk | <0.05 | 0.0089 |
| Compound I 75 mg/kg bid | | Compound I 75 kg/mg bid + Cetuximab 40 mg/kg 2x/wk | <0.05 | 0.0002 |
| Compound I 25 mg/kg bid + Cetuximab 40 mg/kg 2x/wk | | Compound I 75 kg/mg bid + Cetuximab 40 mg/kg 2x/wk | >0.05 | 0.3210 |

*One-Way ANOVA, post-hoc Bonferroni
**Breslow-Gehan-Wilcoxon

Example 6

A suspension comprising Compound I was made in a manner similar to that in Example 1 with the exception that 40 ml of a 3.125 mg/ml suspension was made using 39.6 ml of the vehicle and 429.6 mg of the blend.

Cetuximab was purchased from ImClone Systems, Inc. (available as Erbitux®) as a 2 mg/ml solution. Irinotecan HCl hydrochloride was purchased from Pfizer Inc. (available as Camptosar®) as a stock sterile solution of 20 mg/ml, which was diluted as required with sterile saline to 2 mg/ml.

HT-29 xenograft-containing mice as produced in the manner described in Example 2 were randomized into groups of 10 mice each according to tumor volume so that groups has similar starting mean tumor volumes. The approximate staring mean tumor volume for this study was 135 mm$^3$.

Treatment began on day 11 post-cell implant and ended at day 32 post cell implant. Each group was subjected to a different therapy as follows:

(1) mice receiving Compound I vehicle bid po, cetuximab vehicle 2×/wk ip, and irinotecan HCl vehicle q4d×5 ip;
(2) mice receiving irinotecan HCl at 40 mg/kg q4d×5 ip;
(3) mice receiving Compound I at 25 mg/kg bid po;
(4) mice receiving cetuximab at 40 mg/kg 2×/wk ip;
(5) mice receiving Compound I at 25 mg/kg bid po and irinotecan HCl at 40 mg/kg q4d×5 ip;
(6) mice receiving cetuximab at 40 mg/kg 2×/wk ip and irinotecan HCl at 40 mg/kg q4d×5 ip;
(7) mice receiving Compound I at 25 mg/kg bid po and cetuximab at 40 mg/kg 2×/wk ip;
(8) mice receiving Compound I at 25 mg/kg bid po, cetuximab at 40 mg/kg 2×/wk ip, and irinotecan HCl at 40 mg/kg q4d×5 ip.

The Compound I suspension and its corresponding vehicle were dosed using a sterile 1 cc syringe and 18-gauge gavage needle (0.2 ml/animal) twice daily. Cetuximab and its corresponding vehicle were dosed intraperitoneally using a sterile 1 cc syringe and 26-gauge needle (0.2 ml/animal) twice a week on a Monday/Thursday or Tuesday/Friday schedule. Irinotecan HCl and its corresponding vehicle were dosed intraperitoneally using a sterile 1 cc syringe and 26-gauge needle (0/2 ml/animal) on a q4d×5 schedule. All dosing was based on an average mouse weight of 25 grams.

Tumor measurements were taken once or twice per week. All animals were individually followed throughout the experiment.

Toxicity

Figure 7:
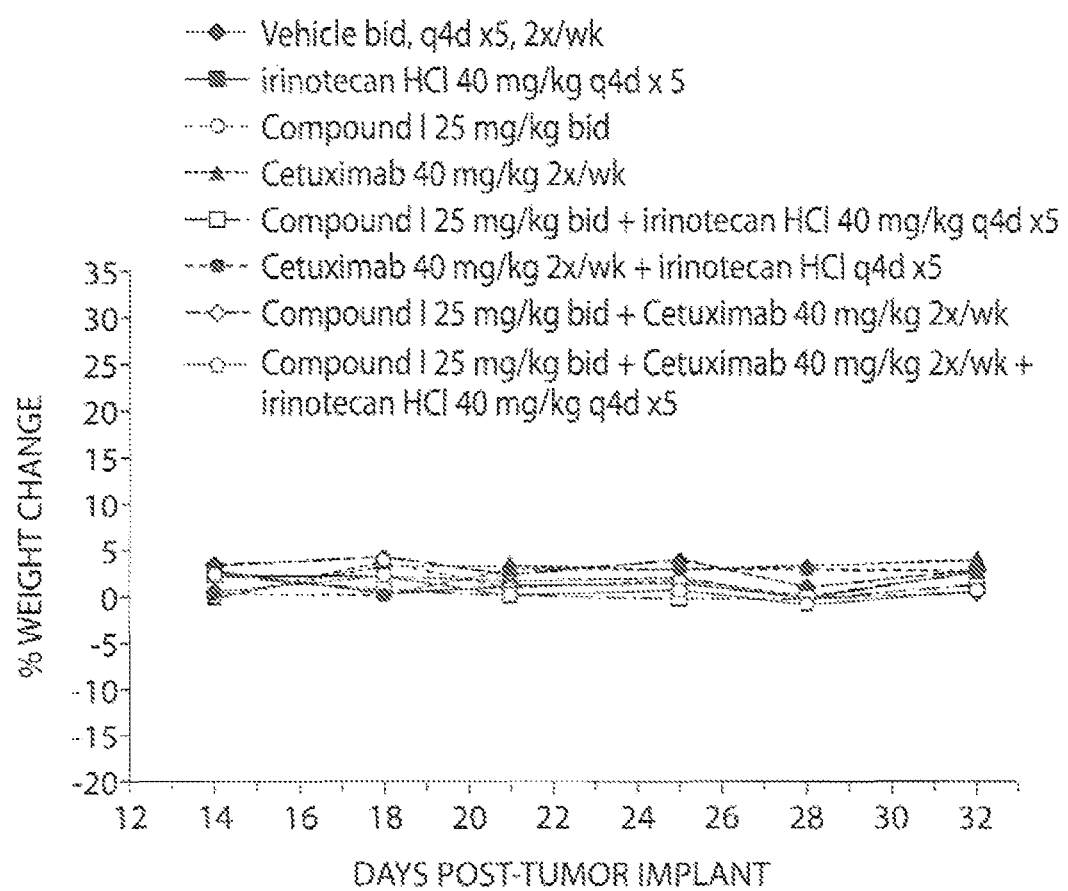
FIG. 7 illustrates the tolerability, as demonstrated by % body weight change, of Compound I monotherapy at 25 mg/kg bid, cetuximab monotherapy at 40 mg/kg 2×/wk, irinotecan HCl monotherapy at 40 mg/kg q4d×5, Compound I at 25 mg/kg bid and irinotecan HCl at 40 mg/kg q4d×5 combination therapy, cetuximab at 40 mg/kg 2×/wk and irinotecan HCl at 40 mg/kg q4d×5 combination therapy, Compound I at 25 mg/kg bid and cetuximab at 40 mg/kg 2×/wk combination therapy, and Compound I at 25 mg/kg bid, cetuximab at 40 mg/kg 2×/wk, and irinotecan HCl at 40 mg/kg q4d×5 combination therapy.

In general, no major signs of toxicity were noted in any dose group in this study described as assessed by measuring changes in body weight and gross observation of individual animals. See Table 11 and FIG. 7. EGFR inhibitor related skin rash was common in cetuximab treated mice with a self-limiting nature even under continuous treatment.

TABLE 11

| Group | Frequency | Route | % Change in Body Weight at end of Study Day 32 | Max % Weight Loss | Max % Weight Gain | # animals ≥ 20% BWL | Mortality |
|---|---|---|---|---|---|---|---|
| Combo Vehicle | bid, 2×/wk, q4d x5 | po, ip, ip | 3.2 | 1.3 | 4.4 | 0 | 0 |
| Irinotecan HCl 40 mg/kg | q4d x5 | ip | 2.7 | 0.1 | 2.8 | 0 | 0 |
| Compound I 25 mg/kg | bid | po | 2.9 | −0.6 | 3.8 | 0 | 0 |
| Cetuximab 40 mg/kg | 2×/wk | ip | 4.0 | 0.1 | 4.0 | 0 | 0 |
| Compound I 25 mg/kg + irinotecan HCl 40 mg/kg | bid, q4d x5 | po, ip | 1.2 | −0.1 | 2.3 | 0 | 0 |
| Cetuximab 40 mg/kg + irinotecan HCl 40 mg/kg | 2×/wk, q4d x5 | ip, ip | 2.8 | 0.2 | 3.2 | 0 | 0 |
| Compound I 25 mg/kg + cetuximab 40 mg/kg | bid, 2×/wk | po, ip | 0.8 | 0.3 | 2.6 | 0 | 0 |
| Compound I 25 mg/kg + cetuximab 40 mg/kg + irinotecan HCl 40 mg/kg | bid, 2×/wk, q4d x5 | po, ip, ip | 0.8 | −0.7 | 2.4 | 0 | 0 |

Tumor Growth Inhibition (TGI)

The group receiving Compound I monotherapy at 25 mg/kg bid exhibited 76% TGI. The group receiving cetuximab monotherapy at 40 mg/kg 2×/wk exhibited 58% TGI. The group receiving irinotecan HCl monotherapy at 40 mg/kg q4d×5 exhibited 59% TGI. The group receiving Compound I at 25 mg/kg bid and irinotecan HCl at 40 mg/kg q4d×5 exhibited 98% TGI. The group receiving cetuximab at 40 mg/kg 2×/wk and irinotecan HCl at 40 mg/kg q4d×5 exhibited 92% TGI. The group receiving Compound I at 25 mg/kg bid and cetuximab at 40 mg/kg 2×/wk exhibited >100% TGI. The group receiving Compound I at 25 mg/kg bid, cetuximab at 40 mg/kg 2×/wk and irinotecan HCl at 40 mg/kg q4d×5 exhibited >100% TGI. No tumor regression was observed with any of the monotherapy groups. The group receiving Compound I at 25 mg/kg bid and cetuximab at 40 mg/kg 2×/wk exhibited 5 out of 10 partial regressions (PRs) but no complete regressions (CRs). The group receiving Compound I at 25 mg/kg bid, cetuximab at 40 mg/kg 2×/wk, and irinotecan HCl at 40 mg/kg q4d×5 exhibited 9 out of 10 PRs and 1 out of 10 CRs.

Figure 8:
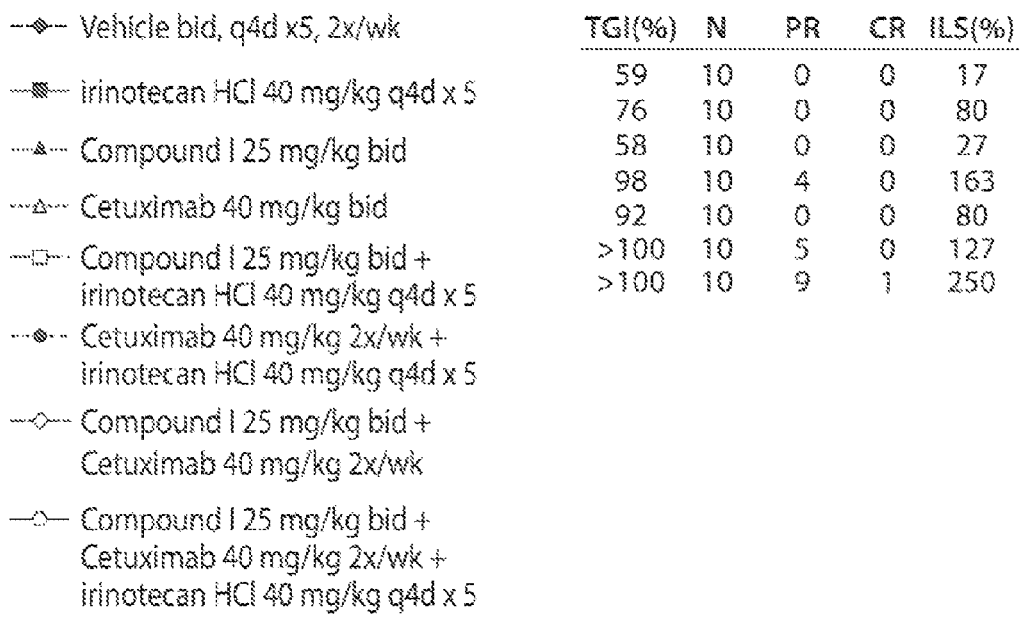
FIG. 8 illustrates the antitumor activity, as demonstrated by the change in mean tumor volume over time, of Compound I monotherapy at 25 mg/kg bid, cetuximab monotherapy at 40 mg/kg 2×/wk, irinotecan HCl monotherapy at 40 mg/kg q4d×5, Compound I at 25 mg/kg bid and irinotecan HCl at 40 mg/kg q4d×5 combination therapy, cetuximab at 40 mg/kg 2×/wk and irinotecan HCl at 40 mg/kg q4d×5 combination therapy, Compound I at 25 mg/kg bid and cetuximab at 40 mg/kg 2×/wk combination therapy, and Compound I at 25 mg/kg bid, cetuximab at 40 mg/kg 2×/wk, and irinotecan HCl at 40 mg/kg q4d×5 combination therapy.
Figure 8:
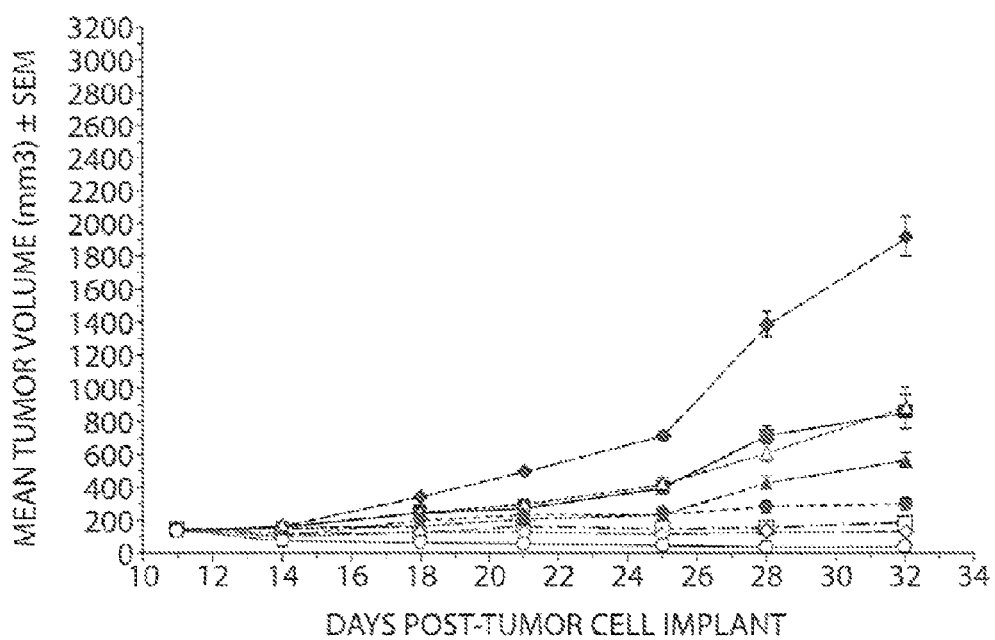

See Tables 12 and 13 and FIG. 8.

TABLE 12

| Group | Frequency | Route | Mean Tumor Volume (mm³) Start Study | SEM | SD | Mean Tumor Volume (mm³) End Study | SD | SEM |
|---|---|---|---|---|---|---|---|---|
| Combo Vehicle | bid, 2×/wk, q4d x5 | po, ip, ip | 133.61 | ±5.44 | ±17.20 | 1920.46 | ±395.43 | ±125.05 |
| Irinotecan HCl 40 mg/kg | q4d x5 | ip | 127.56 | ±4.44 | ±14.03 | 862.41 | ±321.20 | ±101.57 |
| Compound I 25 mg/kg | bid | po | 136.24 | ±6.05 | ±19.13 | 563.72 | ±140.24 | ±44.35 |
| Cetuximab 40 mg/kg | 2×/wk | ip | 132.09 | ±5.80 | ±18.33 | 885.00 | ±406.03 | ±128.40 |
| Compound I 25 mg/kg + irinotecan HCl 40 mg/kg | bid, q4d x5 | po, ip | 144.93 | ±5.35 | ±16.93 | 182.76 | ±69.45 | ±21.96 |
| Cetuximab 40 mg/kg + irinotecan HCl 40 mg/kg | 2×/wk, q4d x5 | ip, ip | 148.52 | ±6.75 | ±21.34 | 295.26 | ±113.09 | ±35.76 |
| Compound I 25 mg/kg + cetuximab 40 mg/kg | bid, 2×/wk | po, ip | 132.52 | ±6.39 | ±20.22 | 122.05 | ±35.99 | ±11.38 |
| Compound I 25 mg/kg + cetuximab 40 mg/kg + irinotecan HCl 40 mg/kg | bid, 2×/wk, q4d x5 | po, ip, ip | 134.61 | ±6.88 | ±21.74 | 40.67 | ±23.89 | ±7.55 |

TABLE 13

| Group | % T/C end of study Day: 32 | % Inhibition end of study Day: 32 | p value End of study Day: 32 | Average % Regression per Group | Partial Regression | Complete Regression | Animals per Group | % Tumor Growth Inhibition |
|---|---|---|---|---|---|---|---|---|
| Combo Vehicle | — | — | — | — | 0 | 0 | 10 | — |
| Irinotecan HCl 40 mg/kg q4d x5 | 41 | 59 | <0.001 | — | 0 | 0 | 10 | 59 |
| Compound I 25 mg/kg bid | 24 | 76 | <0.001 | — | 0 | 0 | 10 | 76 |
| Cetuximab 40 mg/kg 2×/wk | 42 | 58 | <0.001 | — | 0 | 0 | 10 | 58 |
| Compound I 25 mg/kg bid + irinotecan HCl 40 mg/kg q4d x5 | 2 | 98 | <0.001 | — | 4 | 0 | 10 | 98 |
| Cetuximab 40 mg/kg 2×/wk + irinotecan HCl 40 mg/kg q4d x5 | 8 | 92 | <0.001 | — | 0 | 0 | 10 | 92 |
| Compound I 25 mg/kg bid + cetuximab 40 mg/kg 2×/wk | −1 | regression | <0.001 | 8 | 5 | 0 | 10 | >100 |
| Compound I 25 mg/kg bid + cetuximab 40 mg/kg 2×/wk + irinotecan HCl 40 mg/kg q4d x5 | −5 | regression | <0.001 | 70 | 9 | 1 | 10 | >100 |

Assessment of Survival

Figure 9:
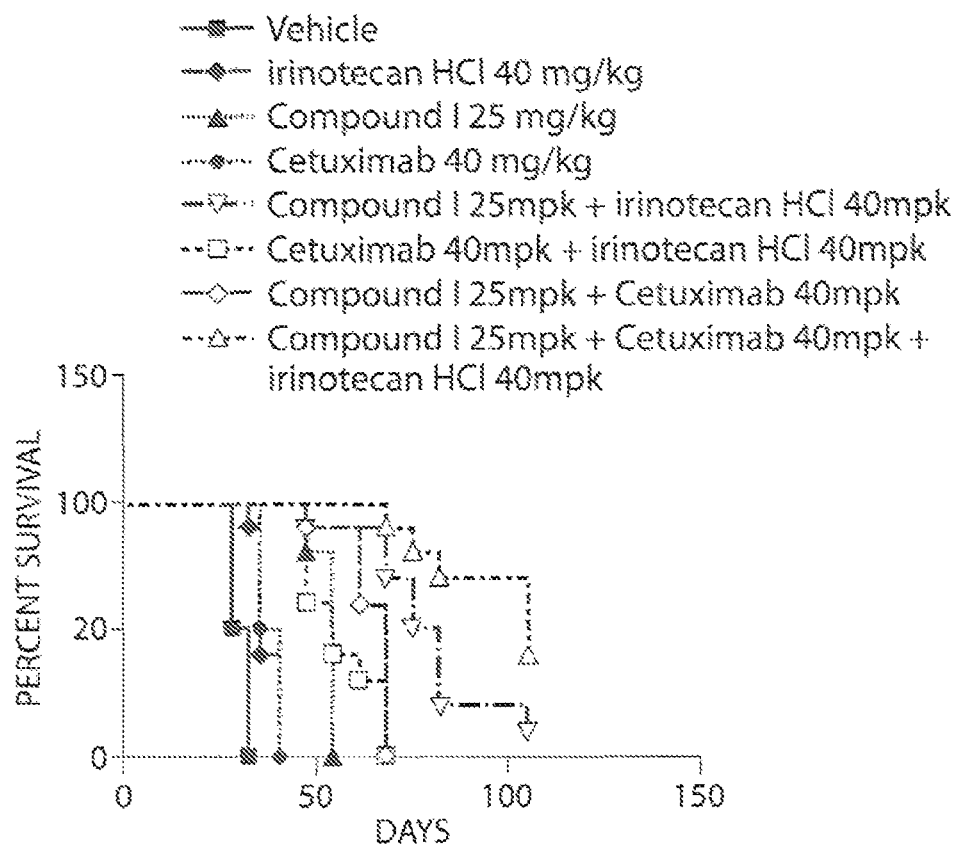
FIG. 9 illustrates the effect on survival, as demonstrated by percentage of surviving mice over time, of Compound I monotherapy at 25 mg/kg bid, cetuximab monotherapy at 40 mg/kg 2×/wk, irinotecan HCl monotherapy at 40 mg/kg q4d×5, Compound I at 25 mg/kg bid and irinotecan HCl at 40 mg/kg q4d×5 combination therapy, cetuximab at 40 mg/kg 2×/wk and irinotecan HCl at 40 mg/kg q4d×5 combination therapy, Compound I at 25 mg/kg bid and cetuximab at 40 mg/kg 2×/wk combination therapy, and Compound I at 25 mg/kg bid, cetuximab at 40 mg/kg 2×/wk, and irinotecan HCl at 40 mg/kg q4d×5 combination therapy.

The group receiving Compound I monotherapy at 25 mg/kg bid exhibited 80% ILS. The group receiving cetuximab monotherapy at 40 mg/kg 2×/wk exhibited 27% ILS. The group receiving irinotecan HCl monotherapy at 40 mg/kg q4d×5 exhibited 17% ILS. The group receiving Compound I at 25 mg/kg bid and irinotecan HCl at 40 mg/kg q4d×5 exhibited 163% ILS. The group receiving cetuximab at 40 mg/kg 2×/wk and irinotecan HCl at 40 mg/kg q4d×5 exhibited 80% ILS. The group receiving Compound I at 25 mg/kg bid and cetuximab at 40 mg/kg 2×/wk exhibited 127% ILS. The group receiving Compound I at 25 mg/kg bid, cetuximab at 40 mg/kg 2×/wk and irinotecan HCl at 40 mg/kg q4d×5 exhibited 259% ILS. See Table 14 and FIG. 9.

TABLE 14

| Group | ILS Calculations | | | |
|---|---|---|---|---|
| | 50% Treatment Days | 50% Vehicle Days | % ILS | p value |
| Combo Vehicle | — | — | — | — |
| Irinotecan HCl 40 mg/kg q4d x5 | 35 | 30 | 17 | <0.0001 |
| Compound I 25 mg/kg bid | 54 | 30 | 80 | <0.0001 |
| Cetuximab 40 mg/kg 2x/wk | 38 | 30 | 27 | <0.0001 |
| Compound I 25 mg/kg bid + irinotecan HCl 40 mg/kg q4d x5 | 79 | 30 | 163 | <0.0001 |
| Cetuximab 40 mg/kg 2x/wk + irinotecan HCl 40 mg/kg q4d x5 | 54 | 30 | 80 | <0.0001 |
| Compound I 25 mg/kg bid + cetuximab 40 mg/kg 2x/wk | 68 | 30 | 127 | <0.0001 |
| Compound I 25 mg/kg bid + cetuximab 40 mg/kg 2x/wk + irinotecan HCl 40 mg/kg q4d x5 | 105 | 30 | 250 | <0.0001 |

Statistical Analysis

The % TGIs of the Compound I/cetuximab, the Compound I/irinotecan HCl, and the Compound I/cetuximab/irinotecan HCl combination therapies were statistically superior to that of all monotherapy arms (p<0.05). The % TGI of the Compound I/cetuximab/irinotecan HCl combination therapy was also statistically superior to that of the Compound I/irinotecan HCl and cetuximab/irinotecan HCl combination therapies (p<0.05).

The % ILSs of the Compound I/cetuximab, the Compound I/irinotecan HCl, and the Compound I/cetuximab/irinotecan HCl combination therapies were statistically superior to that of all monotherapy arms (p<0.05 for all comparisons). The % ILS of the Compound I/cetuximab/irinotecan HCl combination therapy was also statistically superior to that of the Compound I/irinotecan HCl and Compound I/cetuximab combination therapies. See Table 15.

TABLE 15

| Treatment | versus Treatment | TGI p value* | ILS p value** |
|---|---|---|---|
| Irinotecan HCl 40 mg/kg q4d x5 | Compound I 25 mg/kg bid | >0.05 | <0.0001 |
| Irinotecan HCl 40 mg/kg q4d x5 | Cetuximab 40 mg/kg 2x/wk | >0.05 | 0.5370 |
| Irinotecan HCl 40 mg/kg q4d x5 | Compound I 25 mg/kg bid + Irinotecan HCl 40 mg/kg q4d x5 | <0.05 | <0.0001 |
| Irinotecan HCl 40 mg/kg q4d x5 | Irinotecan HCl 40 mg/kg q4d x5 + Cetuximab 40 mg/kg 2x/wk | <0.05 | <0.0001 |
| Irinotecan HCl 40 mg/kg q4d x5 | Compound I 25 mg/kg bid + Cetuximab 40 mg/kg 2x/wk | <0.05 | <0.0001 |
| Irinotecan HCl 40 mg/kg q4d x5 | Compound I 25 mg/kg bid + Cetuximab 40 mg/kg 2x/wk + Irinotecan HCl 40 mg/kg q4d x5 | <0.05 | <0.0001 |
| Compound I 25 mg/kg bid | Cetuximab 40 mg/kg 2x/wk | >0.05 | <0.0001 |
| Compound I 25 mg/kg bid | Compound I 25 mg/kg bid + Irinotecan HCl 40 mg/kg q4d x5 | <0.05 | 0.0004 |
| Compound I 25 mg/kg bid | Irinotecan HCl 40 mg/kg q4d x5 + Cetuximab 40 mg/kg 2x/wk | >0.05 | 0.3457 |
| Compound I 25 mg/kg bid | Compound I 25 mg/kg bid + Cetuximab 40 mg/kg 2x/wk | <0.05 | 0.0004 |
| Compound I 25 mg/kg bid | Compound I 25 mg/kg bid + Cetuximab 40 mg/kg 2x/wk + Irinotecan HCl 40 mg/kg q4d x5 | <0.05 | <0.0001 |
| Cetuximab 40 mg/kg 2x/wk | Compound I 25 mg/kg bid + Irinotecan HCl 40 mg/kg q4d x5 | <0.05 | <0.0001 |
| Cetuximab 40 mg/kg 2x/wk | Irinotecan HCl 40 mg/kg q4d x5 + Cetuximab 40 mg/kg 2x/wk | <0.05 | <0.0001 |
| Cetuximab 40 mg/kg 2x/wk | Compound I 25 mg/kg bid + Cetuximab 40 mg/kg 2x/wk | <0.05 | <0.0001 |
| Cetuximab 40 mg/kg 2x/wk | Compound I 25 mg/kg bid + Cetuximab 40 mg/kg 2x/wk + Irinotecan HCl 40 mg/kg q4d x5 | <0.05 | <0.0001 |
| Compound I 25 mg/kg bid + Irinotecan HCl 40 mg/kg q4d x5 | Irinotecan HCl 40 mg/kg q4d x5 + Cetuximab 40 mg/kg 2x/wk | <0.05 | 0.0006 |
| Compound I 25 mg/kg bid + Irinotecan HCl 40 mg/kg q4d x5 | Compound I 25 mg/kg bid + Cetuximab 40 mg/kg 2x/wk | >0.05 | 0.0030 |
| Compound I 25 mg/kg bid + Irinotecan HCl 40 mg/kg q4d x5 | Compound I 25 mg/kg bid + Cetuximab 40 mg/kg 2x/wk + Irinotecan HCl 40 mg/kg q4d x5 | <0.05 | 0.0420 |
| Irinotecan HCl 40 mg/kg q4d x5 + Cetuximab 40 mg/kg 2x/wk | Compound I 25 mg/kg bid + Cetuximab 40 mg/kg 2x/wk | <0.05 | 0.0862 |
| Irinotecan HCl 40 mg/kg q4d x5 + Cetuximab 40 mg/kg 2x/wk | Compound I 25 mg/kg bid + Cetuximab 40 mg/kg 2x/wk + Irinotecan HCl 40 mg/kg q4d x5 | <0.05 | <0.0001 |

TABLE 15-continued

| Treatment | versus | Treatment | TGI p value* | ILS p value** |
|---|---|---|---|---|
| Compound I 25 mg/kg bid + Cetuximab 40 mg/kg 2x/wk | | Compound I 25 mg/kg bid + Cetuximab 40 mg/kg 2x/wk + Irinotecan HCl 40 mg/kg q4d x5 | >0.05 | <0.0001 |

*One-Way ANOVA, post-hoc Bonferroni
**Breslow-Gehan-Wilcoxon

The invention claimed is:

1. A method of treating a patient suffering from a proliferative disorder, comprising administering to the patient: (A) a first component which comprises, as an active agent, propane-1-sulfonic acid {3-[5-(4-chloro-phenyl)-1H-pyrrolo[2,3-b]pyridine-3-carbonyl]-2,4-difluoro-phenyl}-amide, or a pharmaceutically-acceptable salt thereof; and (B) a second component which comprises, as an active agent, an EGFR inhibitor; the amount of said active agents being such that the combination thereof is therapeutically-effective in the treatment of said proliferative disorder, wherein the proliferative disorder is a tumor comprising b-Raf having the V600E mutation.

2. A method according to claim 1 wherein said proliferative disorder is selected from the group consisting of colorectal cancer, melanoma, and thyroid cancer.

3. A method according to claim 1 wherein said proliferative disorder is colorectal cancer.

4. A method according to claim 1 or claim 3 wherein said propane-1-sulfonic acid {3-[5-(4-chloro-phenyl)-1H-pyrrolo[2,3-b]pyridine-3-carbonyl]-2,4-difluoro-phenyl}-amid, or a pharmaceutically-acceptable salt thereof, is administered in an amount of from about 200 mg/day to about 3000 mg/day.

5. A method according to claim 1 or claim 3 wherein said propane-1-sulfonic acid {3-[5-(4-chloro-phenyl)-1H-pyrrolo[2,3-b]pyridine-3-carbonyl]-2,4-difluoro-phenyl}-amide, or a pharmaceutically-acceptable salt thereof, is administered in an amount of from about 1700 mg/day to about 2100 mg/day.

6. A method according to claim 1 or claim 3 wherein said EGFR inhibitor is erlotinib, or a pharmaceutically acceptable salt thereof.

7. A method according to claim 6 wherein said erlotinib, or a pharmaceutically acceptable salt thereof, is administered in an amount of from about 20 mg/day to about 500 mg/day.

8. A method according to claim 6 wherein said erlotinib, or a pharmaceutically acceptable salt thereof, is administered in an amount of from about 100 mg/day to about 200 mg/day.

9. A method according to claim 1 or claim 3 wherein said EGFR inhibitor is cetuximab.

10. A method according to claim 9 wherein said cetuximab is administered in an amount of from about 50 mg/m$^2$/week to about 700 mg/m$^2$/week.

11. A method according to claim 9 wherein said cetuximab is administered in an amount of from about 200 mg/m$^2$/week to about 500 mg/m$^2$/week.

12. A method according to claim 1 or claim 3 wherein said method further comprises the administration of a third component which comprises, as an active agent, a topoisomerase inhibitor.

13. A method according to claim 12 wherein said topoisomerase inhibitor is irinotecan, or a pharmaceutically acceptable salt thereof.

14. A method according to claim 13 wherein said irinotecan, or a pharmaceutically acceptable salt thereof, is administered in an amount of from about 1 mg/m$^2$/week to about 250 mg/m$^2$/week.

15. A method according to claim 13 wherein said irinotecan, or a pharmaceutically acceptable salt thereof, is administered in an amount of from about 50 mg/m$^2$/week to about 200 mg/m$^2$/week.

16. A method according to claim 1 or claim 3 wherein said propane-1-sulfonic acid {3-[5-(4-chloro-phenyl)-1H-pyrrolo[2,3-b]pyridine-3-carbonyl]-2,4-difluoro-phenyl}-amide, or a pharmaceutically-acceptable salt thereof, is contained in a solid molecular complex with hydroxypropyl methyl cellulose acetate succinate such that it is immobilized in its amorphous form.

17. A method according to claim 16 wherein the amounts of propane-1-sulfonic acid {3-[5-(4-chloro-phenyl)-1H-pyrrolo[2,3-b]pyridine-3-carbonyl]-2,4-difluoro-phenyl}-amide, or a pharmaceutically-acceptable salt thereof, and hydroxypropyl methyl cellulose acetate succinate in said complex are in a ratio of from about 1:9 to about 5:5, respectively.

18. A method according to claim 16 wherein the amounts of propane-1-sulfonic acid {3-[5-(4-chloro-phenyl)-1H-pyrrolo[2,3-b]pyridine-3-carbonyl]-2,4-difluoro-phenyl}-amide, or a pharmaceutically-acceptable salt thereof, and hydroxypropyl methyl cellulose acetate succinate in said complex are in a ratio of about 3:7.

19. A method according to claim 16 wherein said first component comprises a blend wherein about 97% by weight of the blend is said complex and about 3% by weight of the blend is silicon dioxide.

20. A kit comprising: (A) a first component which comprises, as an active agent, propane-1-sulfonic acid {3-[5-(4-chloro-phenyl)-1H-pyrrolo[2,3-b]pyridine-3-carbonyl]-2,4-difluoro-phenyl}-amide, or a pharmaceutically-acceptable salt thereof; and (B) a second component which comprises, as an active agent, an EGFR inhibitor.

21. A kit according to claim 20 further comprising a third component which comprises, as an active agent, a topoisomerase inhibitor.

22. A composition comprising: (A) a first component which comprises, as an active agent, propane-1-sulfonic acid {3-[5-(4-chloro-phenyl)-1H-pyrrolo[2,3-b]pyridine-3-carbonyl]-2,4-difluoro-phenyl}-amide, or a pharmaceutically-acceptable salt thereof; and (B) a second component which comprises, as an active agent, an EGFR inhibitor.

* * * * *